United States Patent [19]

Li et al.

[11] Patent Number: 5,824,533
[45] Date of Patent: Oct. 20, 1998

[54] ORPINOMYCES XYLANASE PROTEINS AND CODING SEQUENCES

[75] Inventors: Xin-Liang Li; Lars G. Ljungdahl; Huizhong Chen, all of Athens, Ga.

[73] Assignee: University of Georgia Research Foundation, Inc., Athens, Ga.

[21] Appl. No.: 445,090

[22] Filed: May 19, 1995

[51] Int. Cl.$^6$ ............................. C07H 21/04; C12N 9/42
[52] U.S. Cl. ...................... 435/209; 536/23.74; 536/23.2
[58] Field of Search ................................. 435/183, 200, 435/205, 201, 209, 69.1, 69.8, 71.1, 320.1, 252.3; 536/23, 74, 23.2

[56] References Cited

U.S. PATENT DOCUMENTS 5,591,619   1/1997   Li et al. .................................... 435/201

FOREIGN PATENT DOCUMENTS

WO94/00578   6/1994   WIPO ............................ C12N 15/56

OTHER PUBLICATIONS

Garcia–Campayo, V. and Wood, T.M., Carbohydrate Research, (1993) 242:229–245.
Gilbert et al (1992), EMBL Submission X 65526/S24754.
Maniatis et al. (1982), *Molecular Cloning*, Cold Spring Harbor Lab, Cold Spring Harbor, NY.
Ali et al. (1995) "Cellulases and hemicellulases of the anaerobic fungus Piromyces constitute a multiprotein cellulose–binding complex and are encodes by multigene families," *FEMS Microbiol. Lett. 125*:15–22.
Barichievich, E.M. and R.E. Calza (1990) "Supernatant protein and cellulase activities of the anaerobic ruminal fungus *Neocallimastix frontalis* EB 188," *Appl. Environ. Microbiol. 56*:43–48.
Borneman et al. (1989) "Fermentation products and plant cell wall–degrading enzymes produced by monocentric and polycentric anaerobic ruminal fungi," *Appl. Environ. Microbiol. 55*:1066–1073.
Chen, H.Z. and L.G. Ljungdahl (May 1993) "Purification and partial characterization of an endoxylanase from the anaerobic polycentric rumen fungus *Orpinomyces* PC–2," Abstract K–129 of American Society for Microbiology Annual Meeting, Atlanta, Georgia.
Chen et al. (1994) "Isolation and properties of an extracellular β–glucosidase from the polycentric rumen fungus *Orpinomyces* sp. strain PC–2," *Appl. Environ. Microbiol. 60*:64–70.
Collins, S.H. (1990) "Production of Secreted Proteins in Yeast," In: *Protein Production by Biotechnology* (Harris, T.J.R. ed.), Elsevier, pp. 61–77.
de Segura, B. G. and M. Fevre (1993) "Purification and characterization of two 1,4–β–xylan encohydrolases from the rumen fungus *Neocallimastix frontalis*," *Appl. Environ. Microbiol. 59*:3654–3660.
Demolder et al. (1992) "Efficient synthesis of secreted murine interleukin –2 by *Saccharomyces cerevisiae*: influence of the 3' untranslated regions and codon usage," *Gene 111*:207–213.

Eriksson et al. (1990) *Microbial and enzymatic degradation of wood and wood components*, Springer–Verlag, New York, NY, pp. 186–213.
Filho et al. (1991) "The xylan–degrading enzyme systems of *Penicillium capsulatum* and *Talaromyces emersonii*," *Biochem. Soc. Trans. 19*:25S.
Garcia–Campayo et al. (1993) "Hydrolysis of oligosaccharide of the β–(1→4)–linked d–xylose series by an endo (1→4)–β–D–xylanase from anaerobic rumen fungus *Neocallimastix frontalis*," *World J. Microbiol. & Biotechnol. 10*:64–68.
Garcia–Campayo, V. and T.M. Wood (1993) "Purification and characterization of a β–D–xylosidase from the anaerobic rumen fungus *Neocallimastix frontalis*," *Carbohydr. Res. 242*:229–245.
Gat et al. (1994) "Cloning and DNA sequence of the gene coding for *Bacillus stearothermophilus* T–6 xylanase," *Appl. Environ. Microbiol. 60*:1889–1896.
Ghangas et al. (1989) "Cloning of a *Thermonospora fusca* xylanase gene and its expression in *Escherichia coli* and *Streptomyces lividans*," *J. Bacteriol. 171*:2963–2969.
Gilkes et al. (1991) "Domains in microbial β–1,4–glycanases: Sequence conservation, function, and enzyme families," *Microbiol. Rev. 55*:303–315.
Hitzeman et al. (1981) "Expression of a human gene for interferon in yeast," *Nature* (London) 293:717–722.
Innis et al. (1985) Expression, glycosylation, and secretion of an Aspergillus glucoamylase by *Sacchromyces cerevisiae*, *Science* 228:21–26.
Kluepfel et al. (1990) "Purification and characterization of a new xylanase (xylanase B) produced by *Streptomyces lividans* 66," *Biochem. J. 267*:45–50.
Kniskern et al. (1991) "Constitutive and regulated expression of the hepatitis B virus (HBV) preS2+S protein in recombinant yeast," In: *Expression systems and processes for rDNA products*, R.T. Hatch, C. Goochee, A. Moreira and Y. Alroy (eds.).
Leathers, T.D. (1989) "Purification and properties of xylanase from Aureobasidium," *j. Ind. Microbiol. 4*:341–348.
Leathers et al. (1986) Induction and glucose repression of xylanase from a color variant strain of *Aureobasidium pullulans*, *Biotechnol. Lett. 8*:867–872.
Leathers, T.D. (1998) Amino acid composition and partial sequence of xylanase from Aureobasidium, *Biotechnol. Lett. 10*:775–780.
Leathers et al. (1984) Overproduction and regulation of xylanase in *Aureobasidium pullulans* and *Cryptococcus albidus*, *Biotechnol. Bioeng. Symp. 14*:225–240.

(List continued on next page.)

*Primary Examiner*—Robert A. Wax
*Assistant Examiner*—Daniel S. Mytelka
*Attorney, Agent, or Firm*—Greenlee, Winner and Sullivan, P.C.

[57] ABSTRACT

Xylanases having high specific activities from Orpinomyces sp. strain PC-2 are provided as well as methods for their purification. DNA sequences encoding these proteins are also provided.

32 Claims, 7 Drawing Sheets

OTHER PUBLICATIONS

Leathers, T.D. (1986) "Color variants of *Aureobasidium pullulans* overproduce xylanase with extremely high specific activity," *Appl. Environ. Microbiol.* 52:1026–1030.

Li et al. (1993) "Purification and characterization of a new xylanase (APX–II) from the fungus *Aureobasidium pullulans* Y–2311–1," *Appl. Environ. Microbiol.* 59:3212–3218.

Li et al. (1992) Regulation and characterization of cellulolytic and xylanolytic enzymes from the polycentric rumen fungus Orpinomyces PC–2. Abstr. 92th Annual Meet. Am. Soc. Microbiol., K–10, p. 285.

Lowe et al. (1987) "Cellulases and xylanases of an anaerobic rumen fungus grown on wheat straw, wheat straw holocellulose, cellulose, and xylan," *Appl. Environ. Microbiol.* 53:1216–1223.

Lüthi et al. (1990) "Cloning, sequence analysis, and expression of genes encoding xylan–degrading enzymes from the thermophile *Caldocellum saccharolyticum*," *Appl. Environ. Microbiol.* 56:1017–1024.

Marten, M. and J–H Seo (1991) "Engineering studies of protein secretion in recombinant *Sacchromyces cerevisiae*," In: *Expression Systems and Processes for rDNA Products* (Hatch, R.T., et al. eds.) pp. 77–95.

Moreau et al. (1992) "Secretion of a *Cryptococcus albidus* xylanase in *Saccharomyces cerevisiae*," *Gene* 116:109–113.

Mounfort, D.O. and R.A. Asher (1989) "Production of xylanase by the ruminal anaerobic fungus *Neocallimastix frontalis*," *Appl. Environ. Micronbiol.* 55:1016–1022.

Shepherd et al. (1981) "Substrate specificity and mode of action of the cellulases from the thermophilic fungus *Thermoascus aurantiacus*," *Biochem J.* 193:67–74.

Simpson et al. (1991) "An extremely thermostable xylanase from the thermophilic eubacterium Thermotoga," *Biochem. J.* 277:413–417.

Teunissen et al. (1993) "Purification and characterization of a complex–bound and a free β–1,4–endoxylanase from the culture fluid of the anaerobic fungus *Piromyces* sp. train E2," *Arch. Microbiol.* 159:265–271.

Tremblay, L. and F. Archibald (1993) "Production of a cloned xylanase in *Bacillus cereus* and its performance in kraft pulp prebleaching," *Can. J. Microbiol.* 39:853–860.

Yang et al. (1992) "The impact of xylanase on bleaching of kraft pulps," *TAPPI J.* 75:95–101.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1221 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( v i ) ORIGINAL SOURCE:
        ( A ) ORGANISM: Orpinomyces
        ( B ) STRAIN: PC-6

( i x ) FEATURE:
        ( A ) NAME/KEY: CDS
        ( B ) LOCATION: 97..1185

( x i ) SEQUENCE DESCRIPTION: SEQ ID NO:1:

```
GGCACGAGGA  AATTTTTTTT  ACTGGTTAAA  AAAAAATTAT  AAAACTAAAT  AAATAAAAAA          60

AATATTTTTT  GAAATATATT  AAAATAGGAA  AAAAAA  ATG  AGA  ACT  ATT  AAA  TTT         114
                                            Met  Arg  Thr  Ile  Lys  Phe
                                             1                 5

TTA  TTC  GCA  TTA  GCT  ATT  ACA  ACC  GTT  GCT  AAG  GCC  CAA  TGG  GGT  GGA  162
Leu  Phe  Ala  Leu  Ala  Ile  Thr  Thr  Val  Ala  Lys  Ala  Gln  Trp  Gly  Gly
               10                      15                      20

AAC  GGT  GGT  GCC  TCT  GCT  GGT  CAA  AGA  TTA  AGC  GTT  GGT  GGT  GGT  CAA  210
Asn  Gly  Gly  Ala  Ser  Ala  Gly  Gln  Arg  Leu  Ser  Val  Gly  Gly  Gly  Gln
          25                      30                      35

AAC  CAA  CAT  AAA  GGT  GTT  TTT  GAT  GGC  TTC  AGT  TAT  GAA  ATC  TGG  TTA  258
Asn  Gln  His  Lys  Gly  Val  Phe  Asp  Gly  Phe  Ser  Tyr  Glu  Ile  Trp  Leu
     40                      45                      50

GAT  AAC  ACC  GGT  GGT  AGT  GGT  TCC  ATG  ACC  CTT  GGT  AAA  GGT  GCA  ACC  306
Asp  Asn  Thr  Gly  Gly  Ser  Gly  Ser  Met  Thr  Leu  Gly  Lys  Gly  Ala  Thr
55                      60                      65                      70

TTC  AAG  GCT  GAA  TGG  AGT  GCA  GCT  GTT  AAC  CGT  GGT  AAC  TTC  CTT  GCC  354
Phe  Lys  Ala  Glu  Trp  Ser  Ala  Ala  Val  Asn  Arg  Gly  Asn  Phe  Leu  Ala
               75                      80                      85
```

```
CGT CGT GGT CTT GAT TTC GGT TCT ACC AAA AAG GCA ACC GCT TAC GAA      402
Arg Arg Gly Leu Asp Phe Gly Ser Thr Lys Lys Ala Thr Ala Tyr Glu
         90              95                 100

TAC ATC GGA TTG GAT TAT GAA GCA AGT TAC AGA CAA ACT GCC AGC GCA      450
Tyr Ile Gly Leu Asp Tyr Glu Ala Ser Tyr Arg Gln Thr Ala Ser Ala
        105             110                 115

AGT GGT AAC TCC CGT CTT TGT GTA TAC GGC TGG TTC CAA AAC CGT GGA      498
Ser Gly Asn Ser Arg Leu Cys Val Tyr Gly Trp Phe Gln Asn Arg Gly
120             125                 130

GTT CAA GGC GTA CCT TTG GTA GAA TAC TAC ATC ATT GAA GAT TGG GTT      546
Val Gln Gly Val Pro Leu Val Glu Tyr Tyr Ile Ile Glu Asp Trp Val
135             140                 145                 150

GAC TGG GTA CCA GAT GCA CAA GGA AAA ATG GTA ACC ATC GAT GGT GCA      594
Asp Trp Val Pro Asp Ala Gln Gly Lys Met Val Thr Ile Asp Gly Ala
                155                 160                 165

CAA TAT AAG ATT TTC CAA ATG GAT CAC ACT GGT CCA ACT ATC AAT GGT      642
Gln Tyr Lys Ile Phe Gln Met Asp His Thr Gly Pro Thr Ile Asn Gly
            170                 175                 180

GGT AAT GAA ACC TTT AAG CAA TAC TTC AGT GTC CGT CAA CAA AAG AGA      690
Gly Asn Glu Thr Phe Lys Gln Tyr Phe Ser Val Arg Gln Gln Lys Arg
        185                 190                 195

ACT TCT GGT CAT ATT ACT GTA TCA GAT CAC TTT AAG GCA TGG TCC AAT      738
Thr Ser Gly His Ile Thr Val Ser Asp His Phe Lys Ala Trp Ser Asn
    200                 205                 210

CAA GGT TGG GGT ATT GGA AAC CTC TAT GAA GTT GCA TTG AAC GCA GAA      786
Gln Gly Trp Gly Ile Gly Asn Leu Tyr Glu Val Ala Leu Asn Ala Glu
215                 220                 225                 230

GGT TGG CAA AGT AGT GGT GTC GCT GAC GTC CCC AAG TTG GAT GTC TAC      834
Gly Trp Gln Ser Ser Gly Val Ala Asp Val Pro Lys Leu Asp Val Tyr
            235                 240                 245

ACC ACC AAA CAA GGT TCT GCT CCT CGT ACT ACC ACC ACT ACC CGT          882
Thr Thr Lys Gln Gly Ser Ala Pro Arg Thr Thr Thr Thr Thr Arg
        250                 255                 260

ACT ACT ACC CGT ACT ACT ACA AAA ACA CTT CCA ACC ACT AAT AAA AAA      930
Thr Thr Thr Arg Thr Thr Thr Lys Thr Leu Pro Thr Thr Asn Lys Lys
    265                 270                 275

TGT TCT GCC AAG ATT ACT GCC CAA GGT TAC AAG TGT TGT AGT GAT CCA      978
Cys Ser Ala Lys Ile Thr Ala Gln Gly Tyr Lys Cys Cys Ser Asp Pro
280                 285                 290

AAT TGT GTT GTT TAC TAC ACT GAT GAA GAT GGT ACC TGG GGT GTT GAA      1026
Asn Cys Val Val Tyr Tyr Thr Asp Glu Asp Gly Thr Trp Gly Val Glu
295                 300                 305                 310

AAC AAT CAA TGG TGT GGA TGT GGT GTT GAA GCA TGT TCT GGC AAG ATT      1074
Asn Asn Gln Trp Cys Gly Cys Gly Val Glu Ala Cys Ser Gly Lys Ile
            315                 320                 325

ACT GCC CAA GGT TAC AAG TGT TGT AGT GAT CCA AAG TGT GTT GTT TAC      1122
Thr Ala Gln Gly Tyr Lys Cys Cys Ser Asp Pro Lys Cys Val Val Tyr
        330                 335                 340

TAC ACT GAT GAC GAT GGT AAA TGG GGT GTT GAA AAC AAC GAA TGG TGT      1170
Tyr Thr Asp Asp Asp Gly Lys Trp Gly Val Glu Asn Asn Glu Trp Cys
    345                 350                 355

GGT TGT GGT TTA TAA GCAGAAAAAT ACTAATTTAG TAAAAAAAAA AAAAAA          1221
Gly Cys Gly Leu *
360
```

( 2 ) INFORMATION FOR SEQ ID NO:2:

( i ) SEQUENCE CHARACTERISTICS:
        ( A ) LENGTH: 362 amino acids
        ( B ) TYPE: amino acid
        ( D ) TOPOLOGY: linear (ii) MOLECULE TYPE: protein (xi) SEQUENCE DESCRIPTION: SEQ ID NO:2:

```
Met Arg Thr Ile Lys Phe Leu Phe Ala Leu Ala Ile Thr Thr Val Ala
 1               5                  10                 15
Lys Ala Gln Trp Gly Gly Asn Gly Gly Ala Ser Ala Gly Gln Arg Leu
                20                 25                 30
Ser Val Gly Gly Gly Gln Asn Gln His Lys Gly Val Phe Asp Gly Phe
            35                 40                 45
Ser Tyr Glu Ile Trp Leu Asp Asn Thr Gly Gly Ser Gly Ser Met Thr
        50                 55                 60
Leu Gly Lys Gly Ala Thr Phe Lys Ala Glu Trp Ser Ala Ala Val Asn
 65                 70                 75                 80
Arg Gly Asn Phe Leu Ala Arg Arg Gly Leu Asp Phe Gly Ser Thr Lys
                85                 90                 95
Lys Ala Thr Ala Tyr Glu Tyr Ile Gly Leu Asp Tyr Glu Ala Ser Tyr
            100                105                110
Arg Gln Thr Ala Ser Ala Ser Gly Asn Ser Arg Leu Cys Val Tyr Gly
            115                120                125
Trp Phe Gln Asn Arg Gly Val Gln Gly Val Pro Leu Val Glu Tyr Tyr
    130                135                140
Ile Ile Glu Asp Trp Val Asp Trp Val Pro Asp Ala Gln Gly Lys Met
145                150                155                160
Val Thr Ile Asp Gly Ala Gln Tyr Lys Ile Phe Gln Met Asp His Thr
                165                170                175
Gly Pro Thr Ile Asn Gly Gly Asn Glu Thr Phe Lys Gln Tyr Phe Ser
            180                185                190
Val Arg Gln Gln Lys Arg Thr Ser Gly His Ile Thr Val Ser Asp His
            195                200                205
Phe Lys Ala Trp Ser Asn Gln Gly Trp Gly Ile Gly Asn Leu Tyr Glu
    210                215                220
Val Ala Leu Asn Ala Glu Gly Trp Gln Ser Ser Gly Val Ala Asp Val
225                230                235                240
Pro Lys Leu Asp Val Tyr Thr Thr Lys Gln Gly Ser Ala Pro Arg Thr
                245                250                255
Thr Thr Thr Thr Thr Arg Thr Thr Thr Arg Thr Thr Thr Lys Thr Leu
            260                265                270
Pro Thr Thr Asn Lys Lys Cys Ser Ala Lys Ile Thr Ala Gln Gly Tyr
            275                280                285
Lys Cys Cys Ser Asp Pro Asn Cys Val Val Tyr Tyr Thr Asp Glu Asp
    290                295                300
Gly Thr Trp Gly Val Glu Asn Asn Gln Trp Cys Gly Cys Gly Val Glu
305                310                315                320
Ala Cys Ser Gly Lys Ile Thr Ala Gln Gly Tyr Lys Cys Cys Ser Asp
                325                330                335
Pro Lys Cys Val Val Tyr Tyr Thr Asp Asp Asp Gly Lys Trp Gly Val
            340                345                350
Glu Asn Asn Glu Trp Cys Gly Cys Gly Leu
            355                360
```

ORPINOMYCES XYLANASE PROTEINS AND CODING SEQUENCES

This invention was made, at least in part, with funding from the U.S. Department of Energy (Grant No. DE-FG05-93ER20127/M001).

FIELD OF THE INVENTION

This invention pertains to a xylanase and a xylanase nucleotide sequence of Orpinomyces sp. Strain PC-2.

BACKGROUND OF THE INVENTION

Hemicellulose, a naturally abundant polysaccharide, consists of xylan as the main constituent. Xylan is a heteropolymer possessing β-1,4 linked xylose units as a backbone with side chains containing pentoses and hexoses, and acetyl groups. Of these groups, some of the arabinoses are esterified by p-coumaric and ferulic acids of lignin [Hartley, R. D., "Phenolic monomers and dimers of plant cell wall and their effects on fiber utilization," In: *Microbial and plant opportunities to improve lignocellulosic utilization by ruminants,* Akin, D. E. et al. (eds.) Elsevier Sci. Publ., Inc., New York (1990) pp. 183–193].

Enzymes, particularly xylanase (EC3.2.1.8) which breaks the backbone of xylan, have received considerable attention for application in industries such as pulp bleaching [Eriksson, K-E. L. (1985) "Swedish developments in biotechnology related to the pulp and paper industry," *TAPPI J.* (Tech. Assoc. Pulp Pap. Ind.) 68:46–55; Jurasek, L. and Paice, M. G. (1988) "Biological bleaching of pulp", In: *International pulp bleaching conference,* TAPPI (Atlanta, Ga.) pp. 11–13; Kantelinen, A. et al. (1988) "Hemicellulases and their potential role in bleaching," In: *International pulp bleaching conference,*" TAPPI (Atlanta, Ga.) pp. 1–9; Noé, P. et al. (1986) "Action of xylanases on chemical pulp fibers. Part II: Enzymatic beating," *J. Wood Sci. Technol.* 6:167–184; and Yang, J. L. et al. (1992) "The impact of xylanase on bleaching of kraft pulps," *TAPPI J.* 75:95–101], pretreatment of animal feed [Wong, K. et al. (1988) "Multiplicity of β-1,4-xylanase in microorganisms. Functions and applications," *Microbiol. Rev.* 52:305–317; and Mandel, M. (1985) "Applications of cellulases," *Biotechnol. Bioeng. Symp.* 13:414–416), food processing [Biely, P. (1985) "Microbial xylanolytic system," *Trends Biotechnol.* 3:286–290, and Dekker, R. F. H. (1979) "The hemicellulase group of enzymes," In: Blanshard, J. M. V. and Mitchell, J. R. (Eds.), *Polysaccharides in Food,* (Butterworths, London) pp. 93–108], and conversion of lignocellulose into feedstock chemicals and fuels [Jeffries, T. W. (1985) "Emerging technology for fermenting D-xylose, " *Trends Biotechnol.* 3:208–212; Mohandas, D. V. et al. (1994) "Development of xylose-fermenting yeasts for ethanol production at high acetic acid concentrations," Sixteenth Symp. on Biotech. for Fuels and Chemicals (Gatlinburg, Tenn.) Paper 16; Lu, Z. and Tsao, G. T. (1994) "Fermentation of xylose to glycerol by fungi," Sixteenth Symp. on Biotech. for Fuels and Chemicals (Gatlinburg, Tenn.) Poster 35].

Enzymatic conversion of xylan to its monomeric components requires the participation of several enzymes including xylanase (EC3.2.1.8), β-xylosidase (EC3.2.1.37), α-L-arabinofuranosidase (EC3.2.1.55), α-glucuronidase (EC3.2.1.1), acetyl xylan esterase (EC3.1.1.6) as well as p-coumaroyl and feruloyl esterases [Borneman, W. S. et al. (1993) "Feruloyl and p-coumaroyl esterases from the anaerobic fungus Neocallimastix MC-2: Properties and functions in plant cell wall degradation," In: *Hemicellulose and Hemicellulases,* M. P. Coughlan and G. Hazelwood, Eds. (Portland Press, Cambridge, U.K.) pp. 85–102; Castanares, A. et al. (1992) "Purification and properties of a feruloyl and p-coumaroyl esterase from the fungus *Penicillium pinophilum,*" *Enzyme Microb. Technol.* 14:875–884; Christov, L. P. and Prior, B. A. (1993) "Esterases of xylan-degrading microorganisms: Production, properties, and significance," *Enzyme Microb. Technol.* 15:460–475; Eriksson, K.-E. L. et al. (1990) "Microbial and enzymatic degradation of wood and wood components," Springer-Verlag (New York, N.Y.)].

Considering the industrial potential of xylanases, an important aspect of xylanase research is to obtain highly active xylanases at low cost. Consequently several bacteria and fungi have been screened for xylanolytic activity [Eriksson, K.-E. L. et al. (1990), supra; Gilkes, N. R. et al. (1991) "Domains in microbial β1,4-glycanase: Sequence conservation, function, and enzyme families," *Microbiol. Rev.* 55:303–315]. All of these microorganisms produce multiple xylanases with varying specific activities. Most of these xylanases are active under restrictive experimental conditions.

The fungus *Aureobasidium pullulans* Y-2311-1 has been shown to produce the highest levels of xylanase among several xylanolytic fungi [Leathers, T. D. (1986) "Color variants of *Aureobasidium pullulans* overproduce xylanase with extremely high specific activity," *Appl. Environ. Microbiol.* 52:1026–1030; Leathers et al. (1986) "Induction and glucose repression of xylanase from a color variant strain of *Aureobasidium pullulans, Biotechnol. Lett.* 8:867–872; Leathers et al. (1984) "Overproduction and regulation of xylanase in *Aureobasidium pullulans* and *Cryptococcus albidus, Biotechnol. Bioeng. Symp.* 14:225–250]. Unfractionated extracellular xylanase from this fungus has been used successfully for the bleaching of kraft pulps [Yang et al. (1992) "The impact of xylanase on bleaching of kraft pulps," *TAPPI J.* 75:95–101). D-Xylose, xylobiose, xylan, and arabinose all induced, while glucose repressed, xylanase production [Leathers, T. D. et al. (1986) *Biotechnol. Lett.* 8:867–872]. Leathers (Leathers, T. D. (1986) *Appl. Environ. Microbiol.* 52:1026–1030] showed that two xylanases with similar molecular masses were secreted into the culture supernatant by *A. pullulans* grown on xylan or xylose, one of which (APX-I) has been purified [Leathers, T. D. (1998) "Amino acid composition and partial sequence of xylanase from Aureobasidium, *Biotechnol. Lett.* 10:775–780; Leathers, T. D. (1989) "Purification and properties of xylanase from Aureobasidium," *J. Ind. Microbiol.* 4:341–348].

Other organisms which produce xylanases include *Streptomyces lividans* (Kluepfel, D., et al. (1990) "Purification and characterization of a new xylanase (xylanase B) produced by *Streptomyces lividans* 66," *Biochem. J.* 267:45–50]; *Thermoascus aurantiacus* [Shepherd, M. G. et al. (1981) "Substrate specificity and mode of action of the cellulases from the thermophilic fungus *Thermoascus aurantiacus,*" *Biochem J.* 193:67–74]; *Thermotoga sp.* strain Fj SS3-B.1 [Simpson, H. D. et al. (1991) "An extremely thermostable xylanase from the thermophilic eubacterium Thermotoga," *Biochem. J.* 227:413–417]; *Penicillium capsulatum* and *Talaromyces emersonii* [Filho, E. X. et al. (1991) "The xylan-degrading enzyme systems of *Penicillium capsulatum* and *Talaromyces emersonii,* " *Biochem. Soc. Trans.* 19:25S]; *Caldocellum saccharolyticum* [Luthi, E. et al. (1990) "Cloning, sequence analysis, and expression of genes encoding xylan-degrading enzymes from the thermophile *Caldocellum saccharolyticum,*" *Appl. Environ. Microbiol.* 56:1017–1024]; *Bacillus stearothermo-*

*philus* [Gat, O. et al. (1994) "Cloning and DNA sequence of the gene coding for *Bacillus stearothermophilus* T-6 xylanase," *Appl. Environ. Microbiol.* 60:1889–1896]; and *Thermonospora fusca* [Ghangas, G. S. et al. (1989) "Cloning of a *Thermonospora fusca* xylanase gene and its expression in *Escherichia coli* and *Streptomyces lividans,"* *J. Bacteriol.* 171:2963–2969].

Yeast (*Saccharomyces cerevisiae*) has been widely used as a host organism for the production of heterologous proteins such as enzymes, structural proteins, hormones, interferons, and cytokines (Collins, S. H., "Production of Secreted Proteins in Yeast," In: *Protein Production by Biotechnology* (Harris, T. J. R. ed.), Elsevier (1990) 61–77; Hitzeman, R. A. et al., "Expression of a human gene for interferon in yeast," *Nature* (London) (1981) 293:717–722; Innis, M. A. et al., "Expression, glycosylation, and secretion of an *Aspergillus glucoamylase* by *Saccharomyces cerevisiae, Science* (1985) 228:21–26; Marten and Seo (1991) "Engineering studies of protein secretion in recombinant *Saccharomyces cerevisiae*," In: *Expression Systems and Processes for rDNA Products* (Hatch, R. T., et al. eds.); Kniskern, P. J. et al., "Constitutive and regulated expression of the hepatitis B virus (HBV) preS2+S protein in recombinant yeast," In: *Expression systems and processes for rDNA products*, R. T. Hatch, C. Goochee, A. Moreira and Y. Alroy (eds.) 1991; and Demolder, J. et al. (1992) "Efficient synthesis of secreted murine interleukin-2 by *Saccharomyces cerevisiae*: influence of the 3' untranslated regions and codon usage," *Gene* 111:207–213). A xylanase gene from *Cryptococcus albidus* has been expressed in *S. cerevisiae* (Moreau, A. et al. (1992) "Secretion of a *Cryptococcus albidus* xylanase in *Saccharomyces cerevisiae,"* *Gene* 116:109–113). Unlike bacteria, yeast do not produce endotoxins, and products from yeast are considered safe for uses in pharmaceutical and food products. Another advantage of using yeast as a host organism for heterologous protein production is that large-scale production and downstream processing of the organism and its products are readily established considering that this organism is the most commonly used organism for fermentation. Moreover, with the advance of molecular biology, genetic manipulation of yeast has become as routine as genetic manipulation of bacteria. Furthermore, most pharmaceutically and industrially important eukaryotic proteins require post-translational modifications during translocation through the endoplasmic reticulum (ER) and cell membrane. These modifications include proper folding, glycosylation, disulfide bond formation, and proteolysis. Yeast has a secretion system similar to higher eukaryotes. Most importantly, proteins secreted into yeast culture medium are protected from aggregation and protease degradation and more easily purified since yeast secrete minimal amounts of proteins into culture medium.

Other organisms have been used for expression of foreign xylanase genes. A *B. subtilis* xylanase gene was expressed in *B. cereus* and used for pretreatment of pulp in a papermaking process. [Tremblay, L. and Archibald, F. (1993) "Production of a cloned xylanase in *Bacillus cereus* and its performance in Kraft pulp prebleaching," *Can. J. Microbiol.* 39:853–860].

Secretion of proteins is facilitated by hydrophobic-residue-rich short signal peptides on the N-terminal regions of protein precursors. Several secreted yeast proteins and peptides including invertase and mating factor a pheromone (α factor) have been shown to possess such signal peptides. These signal peptides are cleaved by specific peptidases during the secretion process. A number of heterologous proteins when fused to these yeast signal peptides are often retained in periplasmic space or secreted into culture medium at low yield [Das, R. C. and Shultz, J. L. (1987) "Secretion of heterologous proteins from *Saccharomyces cerevisiae, Biotechnol. Progress* 3:43–48; Marten and Seo (1991) "Engineering studies of protein secretion in recombinant *Saccharomyces cerevisiae*," In: *Expression Systems and Processes for rDNA Products* (Hatch, R. T., et al. eds.); and Chaudhuri, B. et al. (1992) "The pro-region of the yeast prepro-α-factor is essential for membrane translocation of human insulin-like growth factor 1 in vivo," *Eur. J. Biochem.* 206:793–800].

A critical problem to be solved in order to use xylanase in the industrial applications previously discussed is the production of large quantities of highly active enzymes at low cost. Another problem is the production of enzymes which have high activity over broad temperature and pH ranges, including physiological conditions. The latter properties are particularly important for xylanases in the pretreatment of animal feed.

Thus, a need exists in the art for high-specific-activity xylanases in pure form which degrade hemicellulose, and for DNA encoding these xylanases to enable methods of producing the xylanases in pure form and in large quantities. A need also exists in the art for xylanases which have high activity over a wide range of temperatures and pH, including physiological temperatures and pH.

BRIEF DESCRIPTION OF THE DRAWINGS

FIGS. 3A and 3B illustrate the effects of pH and temperature on Orpinomyces sp. strain PC-2 endoxylanase activity, respectively.

SUMMARY OF THE INVENTION

Figure 1:
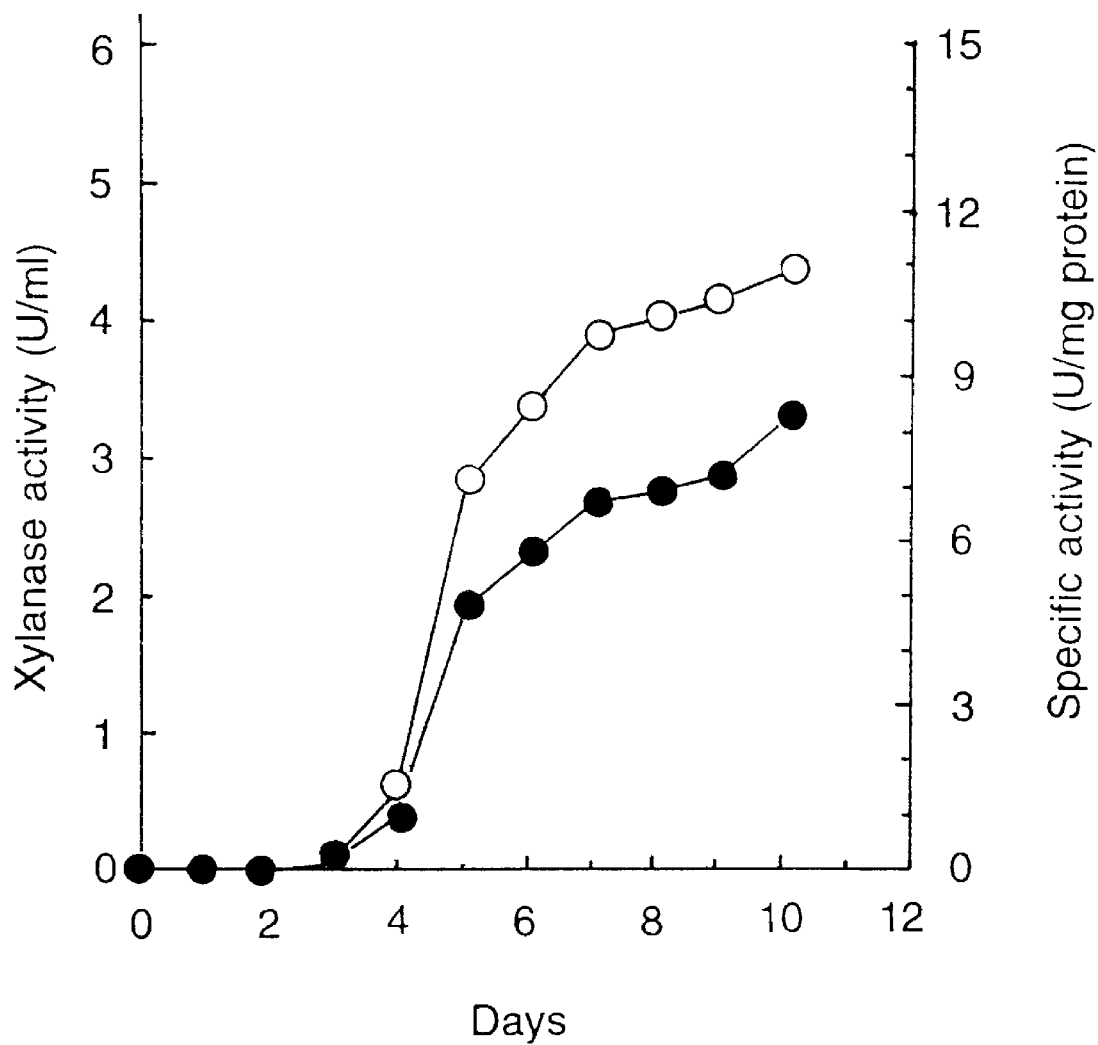
FIG. 1. Time course for xylanase production by Orpinomyces sp. strain PC-2 during growth on sisal fiber at 0.2% (w/v). Filled and open circles represent xylanase activity (U/ml) and specific activity (U/mg protein), respectively.

This invention provides novel xylanases of the anaerobic rumen fungus Orpinomyces sp. strain PC-2. These novel xylanases (XynA-1 and XynA-2) exhibit high specific activity toward a variety of xylan substrates and over broad ranges of pH and temperature. The $K_m$ and $V_{max}$ of XynA-1 on water-soluble oat spelts xylan were 2.15 mg ml$^{-1}$ and 1,770 μmol min$^{-1}$ mg$^{-1}$, respectively. This enzyme is active between pH of 4.6 and 7.0 (optimum between pH 5.5 and 5.8), and at temperatures ranging from about 30° to 60° C. The second enzyme, XynA-2, is active between pH of 4.6 and 7.8 (optimum between pH 5.2 and 7.0), and at temperatures ranging from about 40° to about 70° C. The high specific activity and broad ranges of temperature and pH are attractive properties for a variety of biotechnological applications. The high activity of these enzymes at neutral and slightly acidic pH values and physiological temperatures makes them particularly attractive for use as feed additives for increasing the digestibility of animal feedstocks.

The low apparent masses (29 and 39 kDa for XynA-1 and XynA-2, respectively) and the high pI value (above 8.0) of these enzymes are similar to those of xylanases from *Streptomyces thermoviolaceus* OPC-520 (33 kDa, pI value of 8.0), *Robillarda sp.* Y-20 (17.6 kDa, pI value of 9.7), *S. lividans* 66 (31 kDa, pI value of 8.4), and *Streptomyces roseiscleroticus* (22.6 kDa, pI value of 9.5). All of these xylanases are classified as low-$M_r$, basic xylanases, in contrast to high-$M_r$, acidic xylanases. Most xylanolytic organisms produce both types of xylanases.

This invention provides a substantially pure mature xylanase protein termed "XynA-1" of Orpinomyces sp. strain PC-2, which has a specific activity of about 1600 U/mg protein toward water-soluble xylan (WSX) under the conditions described in Example 1. This invention also provides a substantially pure high-specific-activity xylanase protein termed "XynA-2" of Orpinomyces sp. strain PC-2 and an amino acid sequence as given in SEQ ID NO:2. Both xylanases are useful for degrading hemicellulose, for example, in pulp bleaching in the paper industry, production of ethanol and pretreatment of animal feed.

DETAILED DESCRIPTION OF THE PREFERRED EMBODIMENTS

The following definitions are provided to remove any potential ambiguities as to the intent or scope of their usage in the specification and claims. "Substantially pure" as used herein with respect to XynA-1 or XynA-2 means the protein or polypeptide migrates as a single band on SDS-PAGE as visualized by staining with Coomassie brilliant blue. The protein from Orpinomyces sp. strain PC-2 designated as XynA-1 has a molecular weight of 29 kDa; however the XynA-1 polypeptide of this invention includes proteins or polypeptides having the same or equivalent amino acid sequence and different amounts of glycosylation. The protein from Orpinomyces sp. strain PC-2 designated as XynA-2 has a molecular weight of 39 kDa; however the XynA-2 polypeptide of this invention includes proteins or polypeptides having the same or equivalent amino acid sequence.

The term "XynA-1" refers to the mature protein or polypeptide having a molecular weight of 29 kDa, and $K_m$ and $V_{max}$ values on water-soluble oat spelts xylan of about 2 mg ml$^{-1}$ and 1,770 μmol min$^{-1}$ mg$^{-1}$, respectively, as measured under conditions described in Example 1. "XynA-1" as used herein refers to a polypeptide product which exhibits similar biological activities, i.e., has similar specific activity to natural XynA-1 isolated from Orpinomyces sp. strain PC-2. "Substantially pure" XynA-1 is substantially free of naturally associated components which accompany it in its natural state, either when isolated from Orpinomyces sp. strain PC-2 or when recombinantly produced in host cells.

The term "XynA-2" refers to the protein or polypeptide having the sequence given in SEQ ID NO:2 from amino acid 1 through 362 herein, and equivalent sequences as defined below. "XynA-2" also refers to the mature protein having the sequence given in SEQ ID NO:2 from about amino acid 20 to 25 through amino acid 362 herein, and equivalent sequences as defined below. "XynA-2" as used herein also encompasses a polypeptide product which exhibits similar biological activities, i.e., has similar specific activity to natural XynA-2 isolated from Orpinomyces sp. strain PC-2 or chemically synthesized in accordance with the amino acid sequence provided in SEQ ID NO:2 as measured in recognized bioassays, and has substantially the same or "equivalent" amino acid sequence as native XynA-2 (SEQ ID NO:2). It will be understood that polypeptides deficient in one or more amino acids in the amino acid sequence reported herein for naturally occurring XynA-2, or polypeptides in which one or more amino acids in the amino acid sequence of natural XynA-2 are replaced by other amino acids are within the scope of the invention and have "equivalent" sequences to that given in SEQ ID NO:2, provided that they exhibit the functional activity of XynA-2, e.g. in terms of having high activity over broad ranges of pH (4.6–7.8) and temperature (40°–70°C.). This invention is intended to embrace all the allelic variations of XynA-2. Moreover, as noted above, derivatives obtained by simple modification of the amino acid sequence of the naturally-occurring product, e.g., by way of site-directed mutagenesis or other standard procedures, are included within the scope of the present invention. Forms of XynA-2 produced by proteolysis of host cells that exhibit similar biological activities to naturally-occurring XynA-2 are also encompassed by the present invention. The present specification provides guidance to the skilled worker for preparing a large number of equivalent sequences which preferably do not alter areas of homology shared with other xylanases. "Substantially pure" XynA-2 is substantially free of naturally associated components which accompany it in its natural state, either when isolated from Orpinomyces sp. strain PC-2 or when recombinantly produced in host cells.

A "chemically synthesized" XynA-1 or XynA-2 polypeptide protein is considered an "isolated" protein as is the protein isolated from Orpinomyces sp. strain PC-2 or other host cell in which it is recombinantly produced. The term "chemically synthesized," as related to a sequence of DNA, means that the component nucleotides were assembled in vitro using nonenzymatic means. Manual chemical synthesis of DNA may be accomplished using well established procedures [e.g., M. Caruthers (1983) in *Methodology of DNA and RNA Sequencing*, Weissman (ed.), Praeger Publishers (New York) Chapter 1] or automated synthesis can be performed using one of a number of commercially available machines.

A "recombinant DNA molecule" is one which has been artificially produced from parts derived from heterologous sources, which parts may be naturally occurring or chemically synthesized molecules, and wherein those parts have been joined by ligation or other means known to the art.

"Homology" as used herein refers to identity of nucleotide sequences. The extent of homology between DNA sequences can be ascertained by direct sequencing or can be empirically determined in DNA hybridization experiments, such as those described in B. D. Hames and S. J. Higgins (1985) *Nucleic Acid Hybridization*, IRL Press, Oxford UK.

The amino acids which occur in the amino acid sequence of SEQ ID NO:2 have their usual three- and one-letter abbreviations routinely used in the art, i.e.:

A=Ala=Alanine
C=Cys=Cysteine
D=Asp=Aspartic Acid
E=Glu=Glutamic Acid
F=Phe=Phenylalanine
G=Gly=Glycine
H=His=Histidine
I=Ile=Isoleucine
K=Lys=Lysine
L=Le=Leucine
M=Met=Methionine
N=Asn=Asparagine
P=Pro=Proline
Q=Gln=Glutamine
R=Arg=Arginine
S=Ser=Serine
T=Thr=Threonine
V=Val=Valine
w=Try=Tryptophan
Y=Tyr=Tyrosine This invention also provides for nucleotide sequences encoding the XynA-2 protein or polypeptide. The nucleotide sequence encoding this peptide is termed XynA-2 herein. The XynA-2 cDNA sequence is given in SEQ ID NO:1 from nucleotide 1 through nucleotide 1185. The cDNA sequence encoding the XynA-2 protein is given in SEQ ID NO:1 from nucleotide 97 through nucleotide 1185. The DNA sequence is useful for recombinantly expressing XynA-2 in a variety of host cells including, without limitation, Saccharomyces, Escherichia, Aspergillus, Trichoderma, Aureobasidium, Penicillium, Pichia, Streptomyces and Bacillus. Exemplary species include, for example, *E. coli, Aspergillus nidulans, Aspergillus niger, Aspergillus awamori, Penicillium chrysogenum, Trichoderma reesei, Bacillus subtilis* and *S. cerevisia.*

It is recognized by those skilled in the art that the DNA sequences may vary due to the degeneracy of the genetic code and codon usage. All DNA sequences which code for XynA-2 polypeptide are included in this invention, including DNA sequences as given in SEQ ID NO:1 having an ATG preceding the coding region for the mature protein.

Additionally, it will be recognized by those skilled in the art that allelic variations may occur in the DNA sequences which will not significantly change activity of the amino acid sequences of the proteins which the DNA sequences encode. All such equivalent DNA sequences are included within the scope of this invention and the definition of the XynA-2 protein coding region. The skilled artisan will understand that the amino acid sequence of the exemplified XynA-2 polypeptide can be used to identify and isolate additional, nonexemplified nucleotide sequences which will encode functional equivalents to the polypeptides defined by the amino acid sequences given in SEQ ID NO: 2, or an amino acid sequence of greater than 90% identity thereto and having equivalent biological activity. Nucleotide sequences having at least about 85% homology to the nucleotide sequences of SEQ ID NO:1, from about nucleotide 97 to nucleotide 1185 or functional fragments thereof, and encoding polypeptides with the same function are considered equivalent to the sequences of SEQ ID NO:1 and are included in the definition of "DNA encoding the XynA-2 protein" and the "XynA-2 coding region," respectively. Following the teachings herein, the skilled worker will be able to make a large number of operative embodiments having equivalent DNA sequences to those listed herein.

Homologs of the nucleotide sequence encoding a XynA-2 protein of the present invention may be identified by the ability of their nucleic acids to cross-hybridize under conditions of appropriate stringency as is well understood in the art. It will be understood that there may be minor sequence variations within sequences utilized or disclosed in the present application. A skilled artisan can test allowable variations in sequence, without expense of undue experimentation, by well-known mutagenic techniques which include, but are not limited to, those discussed by D. Shortle et al. (1981) *Ann. Rev. Genet.* 15:265; M. Smith (1985) *Ann. Rev. Genet.* 19:423; D. Botstein and D. Shortle (1985) *Science* 229:1193; by linker scanning mutagenesis (S. McKnight and R. Kingsbury (1982) *Science* 217:316), or by saturation mutagenesis (R. Myers et al. (1986) *Science* 232:613). These variations may be determined by standard techniques in combination with assay methods described herein to enable those in the art to manipulate and bring into utility the various functional units. Using the methods described herein the skilled artisan can without application of undue experimentation test altered sequences within the XynA-2 coding region for retention of function. All such shortened or altered functional sequences of the coding sequences described herein are deemed equivalent thereto and are within the scope of this invention.

Any host cell in which the XynA-2 coding sequence is expressed and processed may be used. A preferred host cell is *S. cerevisiae*, as well as other yeasts known to the art for fermentation, including *Aureobasidum species* and *Pichia pastoris* [Sreekrishna, K. (1993) "Strategies for optimizing protein expression and secretion in the methylotrophic yeast *Pichia pastoris*," in Baltz, R. H., et al. (eds.) Industrial Microorganisms: Basic and Applied Molecular Genetics, ASM Press, Washington, D.C. pp. 119–126; Glick, B. R. and Pasternak, J. J. (1994) "Molecular Biotechnology— Principles and Applications of Recombinant DNA," ASM Press (Washington, D.C.)]. Filamentous fungi such as Aspergillus, Trichoderma, Penicillium, etc. are also useful host organisms for expression of the DNA of this invention. [Van den Handel, C. et al. (1991) "Heterologous gene expression in filamentous fungi," In: Bennett, J. W. and Lasure, L. L. (eds.), More gene manipulations in fungi, Academy Press, Inc. (New York, N.Y.) pp. 397–428]. Bacteria such as *Escherichia coli, Bacillus subtilis* and *Streptomyces lividans* are also useful host organisms.

The present invention also contemplates the use of signal peptides to increase yield of the XynA-2 coding region in host cells in which they are expressed. When DNA encoding a signal peptide operably linked to the XynA-2 coding sequence, the gene product is secreted from the host organism with the help of the signal peptide. Signal peptides direct transport of the protein to its target membrane and are then cleaved by a peptidase on the membrane, such as the endoplasmic reticulum, when the protein passes through it. Signal peptides are well known in the art. A preferred signal peptide is the APX-II signal peptide disclosed in copending U.S. application Ser. No. 08/315,695, filed Sep. 30, 1994, incorporated by reference in its entirety herein. Without wishing to be bound by any theory, it is believed that the coding sequence given in SEQ ID NO:1 from about nucleotide 97 through about nucleotide 154 to 171 may encode a XynA-2 signal peptide, since this region encodes a polypeptide rich in hydrophobic residues, a characteristic of a signal peptide.

In a preferred embodiment, vectors suitable for transformation of the host with the XynA-2 coding region or cDNA coding for the XynA-2 protein are prepared with the gene under control of a promoter expressible in the host. Preferably sequences in SEQ ID NO:1 which are 3' to the coding region for the XynA-2 protein are deleted from such constructs. Promoters can be constitutive or inducible. For example, when the host is a yeast, preferred promoters include, but are not limited to, the yeast enolase promoter [Sangadala et al. (1994) "Preparation and characterization of the site-directed E211Q mutant of yeast enolase," In: *Abstracts of University System of Georgia* 1994 *Research Symposium: Advances in Biotechnology, Georgia State University* (Atlanta, Ga.)] and the yeast alcohol dehydrogenase promoter [Pacitti, A., et al. (1994), "High level expression and purification of the enzymatically active cytoplasmic region of human CD45 phosphatase from yeast," *Biochimica et Biophysica Acta* 1222:277–286]. The vector is used to transform the host either by integration into the chromosome or otherwise. The host organism is then cultured under conditions allowing expression of the gene and the product recovered from the culture medium.

An extracellular endoxylanase was purified to homogeneity from culture filtrate of the strictly anaerobic rumen fungus Orpinomyces sp. strain PC-2. The enzyme, referred to herein as XynA-1, was purifed by Q Sepharose anion-exchange chromatography, CM-Sepharose CL 6B chromatography, Phenyl Superose hydrophobic interaction chromatography, hydroxylapatite chromatography and Superdex™ 75 gel filtration. The enzyme is a monomeric protein with a molecular mass of about 29 kDa as determined by sodium dodecyl sulfate (SDS) polyacrylamide gel electrophoresis, and has a pI of 8.2. The purified enzyme had a $K_m$ of 2.15 mg/ml and a $V_{max}$ of 1,770 $\mu$mol min$^1$ mg$^{-1}$ for water-soluble oat spelts xylan at pH 5.5 and 40° C. The enzyme had pH and temperature optima of 5.4 and 45° C., respectively, and was stable at 45° C. and pH 5.5 for 24 h. It lacked activity towards crystalline cellulose, p-nitrophenyl-β-glucoside, p-nitrophenyl-α-L-arabinoside, p-nitrophenyl-α-xyloside, and p-nitrophenylacetate. The activity of the xylanase was inhibited by N-bromosuccinimide, p-hydroxymercuribenzoate, SDS, Ag$^+$, Cu$^{2+}$, Hg$^{2+}$, and Fe$^{2+}$. As discussed in Example 1 below, xylanase activity was detected in high molecular mass complexes from the eluted protein fractions which had estimated masses of up to about 2 million Da.

The xylanases of the present invention are believed to be among the most active known endo-acting polysaccharide hydrolases. The anaerobic fungus Orpinomyces sp. strain PC-2 grows well on a variety of polysaccharides and simple sugars, with sisal fiber, coastal Bermudagrass (CBG) and corn fiber being the most effective inducers of xylanase. Xylose and Avicel™ also induce xylanase. Low constitutive levels of xylanase are present in cultures grown on glucose. These results suggest that the xylanases of Orpinomyces sp. strain PC-2 are both constitutive and inducible, similar to the xylanases of other anaerobic fungi [Williams, A. G. and Orpin, C. G. (1987) "Polysaccharide-degrading enzymes formed by three species of anaerobic rumen fungi grown on a range of carbohydrates," *Can. J. Microbiol.* 33:418–426; Lowe, S. E., et al. (1987) "Cellulases and xylanases of an anaerobic rumen fungus grown on wheat straw, wheat straw holocellulose, cellulose, and xylan," *Appl. Environ. Microbiol.* 53:1216–1223; Mountfort, D. O. and Asher, R. A. (1989) "Production of xylanase by the ruminal anaerobic fungus *Neocallimastix frontalis,*" *Appl. Environ. Microbiol.* 55:1016–1022; and Teunissen, M. J., et al. (1992) "Purification and characterization of an extracellular β-glucosidase from the anaerobic fungus *Piromyces sp.* strain E2," *Arch. Microbiol.* 158:276–281].

Hg$^{2+}$ cation strongly inhibits the activity of XynA-1, suggesting the presence of thiol (—SH—) or histidine residues at the active site [Simpson, R. B. (1961) "Association constant of methylmercury with sulfydryl and other bases," *J. Am. Chem. Soc.* 84:4711–4717]. Enzymic activity was completely inhibited by 1 mM N-bromosuccinimide, which suggests that at least one tryptophan residue is essential to activity. Xylanases from other microbial strains also reportedly possess essential tryptophan residues at their active sites [Bastawde, K. B. (1992) "Xylan structure, microbial xylanases, and their mode of action," *World J. Microbiol. Biotechnol.* 8:353–368; Filho, E. X. F., et al. (1993) "Physicochemical and catalytic properties of a low-molecular-weight endo-1,4-β-D-xylanase from *Myrothecium verrucaria,*" *Enzyme Microb. Technol.* 15:535–540]. These tryptophan residues are apparently conserved in xylanases, indicating the importance of tryptophan for the function of the enzyme [see Bastawde (1992), supra]. The inhibition by p-hydroxymercuribenzoate (pHMB) further suggests that a cysteine residue or residues is required for activity or to maintain the three-dimensional structure of the active site [Bastawde (1992), supra; Filho et al. (1993), supra]. The XynA-1 xylanase is extremely sensitive to SDS; less than 1 mM SDS causes total inactivation.

The XynA-l protein from Orpinomyces sp. strain PC-2 lacks activity towards crystalline cellulose, carboxymethyl cellulose (CMC), and glycosides, even after a long incubation period (up to 10 hr) at high concentrations, which suggests that it is a true endoxylanase. Xylanases from microorganisms differ widely in their affinities towards xylan. $K_m$ values, for example, vary from a low of 0.14 mg/ml for *Trichoderma reesei* Xyn2 [Torronen, A., et al. (1992) "The two major xylanases from *Trichoderma reesei*: characterization of both enzymes and genes," *Biotechnology* 10: 1461–1465] to 7.6 mg/ml for *Aureobasidium pullulans* [Li, X-L., et al. (1993) "Purification and characterization of a new xylanase (APX-II) from the fungus *Aureobasidium pullulans* Y-2311-1,*" Appl. Environ. Microbiol.* 59:3212–3218]. $K_m$ values for bacterial xylanases are even more variable [Keskar, S. S., et al. (1989) "Chemical modification of a xylanase from a thermotolerant Streptomyces T7, "*Biochem. J.* 261:49–55].

Based on end-product analysis (see Table 5 and FIG. 4), XynA-1 is an endoxylanase that randomly cleaves the glycosidic linkages in the xylan-backbone in an endo fashion; it does not split L-arabinosyl-initiated branch points. This enzyme is thus a non-debranching endoxylanase [Dekker, R. F. H. and Richards, G. N. (1976) "Hemicellulases: their occurrence, purification, properties, and mode of action," *Adv. Carbohydr. Chem. Biochem.* 32:277–352].

Figure 5:
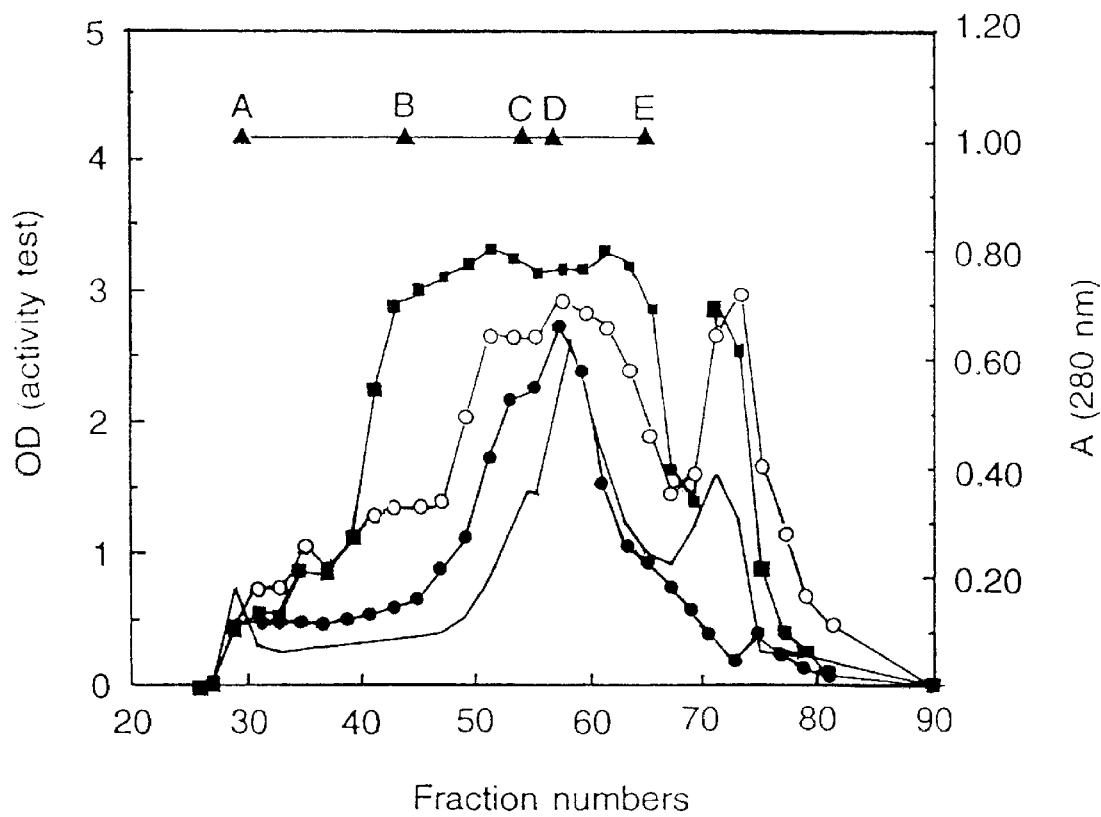
FIG. 5. Protein and hydrolytic enzyme activity from preparations of Orpinomyces sp. strain PC-2 mycelia grown on Avicel substrate and eluted with water and buffer on a Superose 6B column. The column was equilibrated and run with 10 mM sodium phosphate (pH 6.0) containing 0.3M NaCl. The concentrated enzyme preparations (200-$\mu$l) were injected into the column through a sample loop. The flow rate was 0.3 ml min$^{-1}$ and the fraction size was 0.3 ml. A: dextran (2,000 kDa); B: thyroglobulin (669 kDa); C: catalase (232 kDa), D: BSA (66 kDa); E: chymotrypsinogen A (25 kDa). Filled and open circles represent β-glucosidase and CMCase, respectively. Filled squares and filled triangles represent xylanase and $M_r$, respectively.

As evident from the examples herein, the recovery of XynA-1 from the supernatant of Orpinomiyces sp. strain PC-2 is relatively difficult and requires an extensive purification scheme, including several complex chromatography steps. FIG. 5 shows the complex chromatographic profiles of protein, xylanase, CMCase and B-glucosidase for Avicel-grown preparations of Orpinomyces PC-2.

In a second embodiment of the invention, an extracellular endoxylanase (referred to herein as XynA-2) was obtained using recombinant techniques. Orpinomyces sp. strain PC-2 was isolated from the rumen of a cow and cultured as described by Borneman, W.S., et al. (1989) "Fermentation products and plant cell wall degrading enzymes produced by nomocentric and polycentric anaerobic fungi," *Appl. Environ. Microbiol.* 55:1066–1073. The XynA-2 coding sequence was cloned from a cDNA library using an expression screening method, sequenced and ultimately expressed in *Escherichia coli*. This recombinant xylanase has high activity at broad ranges of pH (5.0 to 7.8) and temperature (40°–70° C.), similar to the purified XynA-1 xylanase described above.

The amino acid sequence of XynA-2 and the nucleotide sequence encoding this enzyme (XynA-2 coding region) are shown in SEQ ID NOS:1 and 2. A putative translation start codon (ATG) at nucleotide 97 begins an open reading frame (ORF) which encodes a polypeptide of 362 amino acids. The G+C content of the coding region is 42%, while the non-coding 5' and 3' regions are extremely A+T rich. The encoded polypeptide has a predicted molecular mass of about 39 kD. The N-terminal region of this polypeptide is rich in hydrophobic residues, which may function as a membrane translocation signal peptide and may be removed from the mature xylanase during synthesis.

The XynA-2 has two conserved C-terminal repeated domains which are homologous to the corresponding regions of the *Neocallimastix patriciarum* xylanase [Gilbert, H. J. et al. (1992) "Homologous catalytic domains in a rumen fungal xylanase: evidence for gene duplication and prokaryotic origin," *Mol. Microbiol.* 6:2065–2072] and an endoglucanase [Zhou, L. P., et al. (1994) "Intronless celB from the anaerobic fungus *Neocallimastix patriciarum* encodes a modular family A endoglucanase," *Biochem. J.* 297:359–364].

The XynA-2 coding region was expressed in *Escherichia coli* using plasmid pOX8. Over 70% of total xylanase activity was recovered in the periplasmic fraction, indicating that the mature enzyme is secreted into the periplasmic space of *E. coli*. To further increase expression levels, the Orpinomyces XynA coding region was inserted in frame into pRSET plasmid comprising a T7 promoter. To facilitate the in-frame insertion, the XynA coding region was amplified using polymerase chain reaction (PCR) with two primers containing EcoRI and BamHI restriction sites. The latter clone produced a 10-fold increase in xylanase activity over pOX8 after induction with IPTG.

It will be apparent to those of ordinary skill in the art that alternative methods, reagents, procedures and techniques other than those specifically detailed herein can be employed or readily adapted to produce the xylanases and practice the methods of this invention. Such alternative methods, reagents, procedures and techniques are within the spirit and scope of this invention.

The proteins and methods of this invention are further illustrated in the following non-limiting Examples. All abbreviations used herein are standard abbreviations in the art. Specific procedures not described in detail in the Examples are well-known in the art.

EXAMPLES

Example 1
Purification and Characterization of XynA-1

Chemicals: Reagents for the cultivation of Orpinomyces sp. strain PC-2 were purchased from Difco Lab. (Detroit, Mich.). Resins for liquid chromatography and gel filtration calibration markers were purchased from Pharmacia LKB Biotechnology (Piscataway, N.J.). Reagents and standard markers for gel electrophoresis and immunoblot analysis were purchased from Bio-Rad Lab. (Richmond, Calif.). Immobilon-P membranes for immunoblot analysis were obtained from Millipore Co. (Bedford, Mass.). All other chemicals were products of Sigma Chemical Co. (St. Louis, Mo.).

Strain and cultivation conditions: Orpinomyces sp. strain PC-2 isolated from a cow rumen was maintained in 50 ml serum bottles with a gas phase of 100% $CO_2$. Cultures were transferred every 5 days on medium containing 0.3% Avicel PH-101 (Microcrystalline cellulose, type 101; FMC Corp., Philadelphia, Pa.), as described in Borneman, W. S., et al. (1989) "Fermentation products and plant cell wall degrading enzymes produced by monocentric and polycentric anaerobic rumen fungi," *Appl. Environ. Microbiol.* 55:1066–1073. Xylanase studies were carried out in 150 ml serum bottles containing 100 ml basic medium, as described by Barichievich, E. M. and Calza, R. E. (1990) "Supernatant protein and cellulase activities of the anaerobic ruminal fungus *Neocallimastix frontalis* EB188," *Appl. Environ. Microbiol.* 56:43–48. Small samples of supernatant were withdrawn daily for analysis. The culture filtrate was centrifuged and the supernatant was used for assays of enzymes, soluble protein, and reducing sugars.

The effect of substrate concentration on xylanase production of Orpinomyces sp. strain PC-2 were tested. The highest production of xylanase occurred between 0.15% and 0.25% (w/v) substrate. Based on these results, subsequent xylanase studies employed 0.2% substrate.

As shown in FIG. 1, secretion of xylanase into the culture medium began 3 days after inoculation. The level of the enzyme activity increased steadily until day 7 and continued to increase slowly until day 10. At this time, autolysis of fungal mycelia occurred and intracellular enzyme was released into the culture. An 8-day sample was used for the enzyme purification, discussed below (results shown in Table 2). The crude supernatant had xylanase activity of 2.9 U $ml^{-1}$ and specific activity of 11.2 U $mg^{-1}$.

As shown in Table 1, Orpinomyces sp. strain PC-2 grown on different substrates produced different levels of xylanase. Sisal fiber, coastal Bermudagrass (CBG), and corn fiber produced the highest amounts and activities of xylanase. Xylose also induced a high amount of xylanase. Sisal fiber was used as substrate for large scale enzyme production since it provided high specific activity and efficient separation of the supernatant from the residual substrate and fungal mycelia.

TABLE 1

Effect of Substrate on Xylanase Production by Orpinomyces p. strain PC-2

| Substrate[a] | Xylanase[b] | |
|---|---|---|
| | U $ml^{-1}$ | U $mg^{-1}$ |
| Glucose | 0.42 | 1.31 |
| Xylose | 1.94 | 6.07 |
| Cellobiose | 0.41 | 1.64 |
| Starch | 0.53 | 1.96 |
| Avicel | 1.66 | 7.74 |
| Xylan | 0.89 | 3.52 |
| Corn fiber | 2.33 | 4.69 |
| Coastal Bermudagrass | 2.85 | 5.76 |
| Sisal Fiber | 2.69 | 9.78 |

[a]Substrate concentration 0.2% (wt $vol^{-1}$).
[b]Xylanase levels in culture media after 7-day incubation.

TABLE 2

Purification of Xylanase from Orpinomyces sp. strain PC-2

| Step | Total Protein (mg) | Total U | Specific Activity (U mg$^{-1}$ protein) | Yield (%) | Purification (fold) |
|---|---|---|---|---|---|
| Supernatant | 3613.8 | 40475 | 11.2 | 100 | 1 |
| Concentrate | 2575.7 | 36832 | 14.3 | 91 | 1.3 |
| Q-Sepharose | 334.3 | 11900 | 35.6 | 29.4 | 3.2 |
| CM Sepharose | 125.1 | 8418.8 | 67.3 | 20.8 | 6.0 |
| Phenyl-Superose | 23.9 | 5868.9 | 245.6 | 14.5 | 21.9 |
| Hydroxyapatite | 2.48 | 1821.4 | 733.2 | 4.5 | 65.5 |
| Superdex 75 | 0.83 | 1295.2 | 1560.5 | 3.2 | 139.3 |

Large Scale Fermentation for XynA-1 Production: Orpinomyces sp. strain PC-2 was grown at 39° C. for 8 days in 20-liter vessels, each containing 14 liters of basal medium [Barichievich and Calza (1990), supra] and 28 g (0.2%) of sisal fiber. The medium was autoclaved 1 h, after which cysteine-HCl (0.03%) was added. The medium was then cooled under a stream of CO$_2$. Penicillin (334 U ml$^{-1}$), streptomycin sulfate (80 μg ml$^{-1}$), and chloramphenicol (10 μg ml$^{-1}$) were filter sterilized (0.22 μm filter unit; Millipore Products Division, Bedford, Mass.) and added to the sterile medium just prior to inoculation. Cultures were transferred at least twice. After 72 hr incubation, each vessel was inoculated with 400 ml of culture.

Enzyme assays: All enzyme assays were carried out in duplicate and in 50 mM piperazine/HCl buffer at pH 5.5 and 40° C. unless otherwise stated.

a. Xylanase activity was assayed by mixing a 0.2 ml aliquot of diluted enzyme with 0.4 ml buffer containing 1.0% (w/v) oat spelt xylan (Sigma Chemical Co., St. Louis, Mo.), preheated to 40° C. After 15 min at 40° C., the reaction was terminated by the addition of 1.2 ml of 3,5-dinitrosalicylic acid (DNS) (Miller, 1959), followed by 0.2 ml of 2.5N NaOH to dissolve the residual water-insoluble xylan. The reaction tube was then placed in boiling water for 5 min before determining the absorbance at 550 nm (A550 nm). Xylose was used as the standard.

b. Cellulase activity was assayed with Avicel (type 101) and carboxymethyl cellulose (CMC; sodium salt, low viscosity, Sigma) as substrates. With Avicel, 0.25 ml of enzyme solution was incubated with 5 mg of the substrate in 0.5 ml buffer for 4 h. The reaction was terminated by addition of 1.5 ml DNS reagent and boiled for 5 min. The sample was centrifuged to remove residual Avicel, then assayed at A550 nm. The assay was similar using CMC as substrate, expect for a 30 min incubation time and no centrifugation step. Other substrates were tested under the CMC conditions. Glucose was used as the standard.

c. Activity on p-nitrophenyl (PNP)-linked substrates was assayed by mixing a 0.1 ml aliquot of diluted enzyme with 0.3 ml of 4 mM buffer containing PNP-linked substrate and incubating for 10 min. The reaction was stopped by the addition of 1M 0.8 ml Na$_2$CO$_3$. The liberated p-nitrophenol (PNP) was measured spectrophotometrically at 405 nm, as described in Herr, D. et al. (1978) "Purification and properties of an extracellular 0β-glucosidase from Lenzites trabea," *Appl. Microbiol. Biotechnol.* 5:29–36.

One unit (U) of enzyme activity was defined as the amount of enzyme required for the hydrolysis of one μmol of substrate per min. Specific activity was expressed as units per milligram of protein.

Enzyme purification: Orpinomyces sp. strain PC-2 cultures were grown for 8 days, then filtered (50 mesh nylon net) to remove residual sisal fiber and fungal mycelia. The filtrate was concentrated 200 fold and dialyzed against 20 liters of 10 mM piperazine-HCl buffer (pH 5.5) using a 10 kDa cutoff cassette (Millipore, Bedford, Mass.). The final concentrate (350 ml) was centrifuged at 20,000×g for 20 min to remove precipitated material. The concentrated supernatant was loaded onto a Q Sepharose Fast Flow column (2.6×50 cm; Pharmacia Fine Chemicals, Uppsala, Sweden). Proteins were eluted first with 200 ml of 10 mM piperazine-HCl buffer (pH 5.5) to remove unabsorbed protein. This first protein fraction contained about 32% of the total xylanase activity, with almost no β-glucosidase activity. Bound proteins were then eluted with 500 ml of 1M NaCl. This second protein fraction contained about 50% of the total xylanase activity, and most of the β-glucosidase and carboxymethyl-cellulase (CMCase) activities. The unabsorbed (first) protein fractions were collected and concentrated to about 30 ml by ultrafiltration (Amicon Co., Beverly, Mass.) using a PM 10 membrane. Concentrated fractions were subjected to three cycles of dilution and concentration using 10 mM sodium acetate, pH 5.0. The buffered concentrate was loaded onto a CM Sepharose CL×6B column (2.6×15 cm; Pharmacia, Piscataway, N.J.) equilibrated with 10 mM sodium acetate, pH 5.0. Proteins were eluted first with 100 ml of 10 mM sodium acetate (pH 5.0) to remove unabsorbed protein, then with 500 ml of NaCl gradient (0 to 0.5M) in the same buffer. Residual CMCase activity was removed by this step. Fractions containing the main peak of xylanase were pooled and concentrated by ultrafiltration to about 20 ml. Concentrated fractions were subjected to three cycles of dilution and concentration using 10 mM sodium phosphate, pH 7.0. Solid ammonium sulphate was then added to bring the concentration to 1.6M. The sample was loaded on a Phenyl Superose 5/5 column equilibrated with 10 mM sodium phosphate containing 1.6M ammonium sulphate. Xylanase activity was eluted with a 30 ml linear gradient of ammonium sulphate, from 1.6 to 0M. The active fractions of xylanase were pooled and dialyzed for 24 h at 4° C. against 1000 ml of a 1 mM sodium phosphate, pH 7.0 (changing 4 times) solution containing 0.02% (w/v) NaN$_3$. A hydroxyapatite (HA) column (5×15 cm; Bio-Rad, Richmond, Calif.) was equilibrated with 1 mM sodium phosphate buffer. The dialyzed and buffered samples were then loaded on the column and eluted with 500 ml of a NaCl gradient (0 to 0.2M). Fractions containing high xylanase activity were pooled and concentrated by ultrafiltration. The sample was further concentrated to 0.6 ml using a Centricon 10 (Amicon, Inc., Beverly, Mass.). Final purification was achieved by gel filtration on Superdex 75 10/30 column (Pharmacia) equilibrated with 10 mM sodium phosphate, pH 6.0, containing 0.3 M NaCl. 200 μl aliquots of enzyme solution were loaded on the column. Fractions of 0.3 ml were collected and those containing xylanase activity were combined and stored at −20° C. The purified xylanase had a specific activity of 1295 U mg$^{-1}$ of protein.

Analytical method: Sodium dodecyl sulfate-polyacrylamide gel electrophoresis (SDS-PAGE) was performed as described in Laemmli, U. K. (1970) "Cleavage of structural proteins during the assembly of the head of bacteriophage T4," *Nature* 227:680–685, using 12% polyacrylamide. Low molecular weight protein standards (Bio-Rad, Richmond, Calif.) were used as markers. Electrophoresis was performed using a Mini-PROTEIN II Cell (Bio-Rad, Richmond,Calif.). Gels were stained with Coomassie brilliant blue R 250 according to Fairbanks, G., et al. (1971) "Electrophoretic analysis of the major polypeptides of the human erythrocyte membrane," *Biochemistry* 10:2606–2616. Analytical isoelectric focussing was performed on a Phast System™ (Pharmacia) using a carrier ampholyte (pH 3-9) according to manufacturer's instructions.

Figure 2:
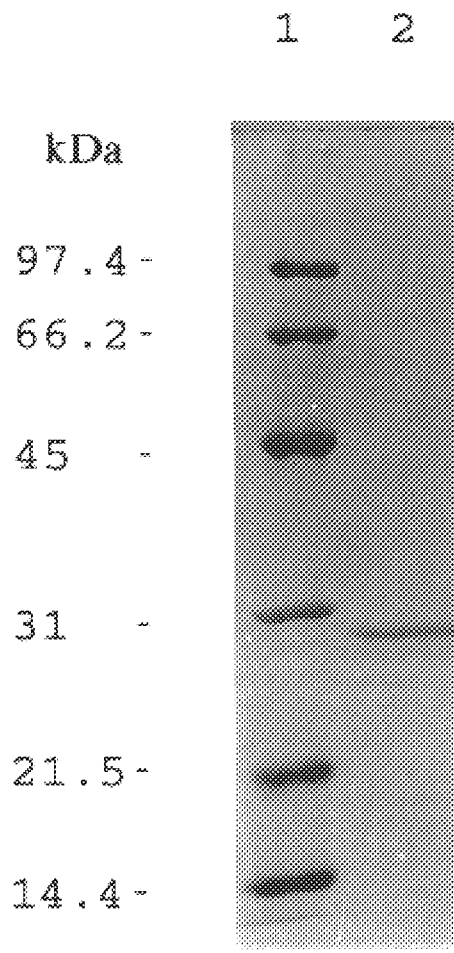
FIG. 2. SDS-PAGE of the purified endoxylanase. Lane 1, molecular mass of protein standards: lysozyme (14.4 kDa); soybean trypsin inhibitor (21.5 kDa); carbonic anhydrase (31 kDa); ovalbumin (45 kDa); BSA (66.2 kDa), and phosphorylase b (97.4 kDa). Lane 2, purified endoxylanase (1 $\mu$).

The purified xylanase appeared as a single band on SDS-PAGE. The protein has an apparent molecular weight of 29 kDa (FIG. 2), $M_r$ of approximately 27,000, and an isoelectric point of 8.2. XynA-1 is believed to be a monomeric protein. Efforts to sequence the N-terminus of the XynA-1 protein were unsuccessful, possibly because the N-terminus is blocked. Chen, H., et al. (1994), "Isolation and Properties of an extracellular β-glucosidase from the polycentric rumen fungus Orpinomyces sp. strain PC-2," *Appl. Environ. Microbiol.* 60:64–70, reports similar results with a β-glucosidase from the same fungal strain.

Water-soluble and insoluble xylan fractions were prepared from oat spelts xylan by suspending 8% whole xylan (w/v) in water. The suspension was stirred for 8 h at 20° C., then centrifugated at 16,000×g for 10 min. The supernatant and pellet were separated and freeze dried, as described by Matte, A., and Forsberg, C. W. (1988) "Isolation and Characterization, and mode of action of endoxylanases 1 and 2 from *Fibrobacter succinogenes* S85," *Appl. Environ. Microbiol.* 58:157–168.

Figure 3A:
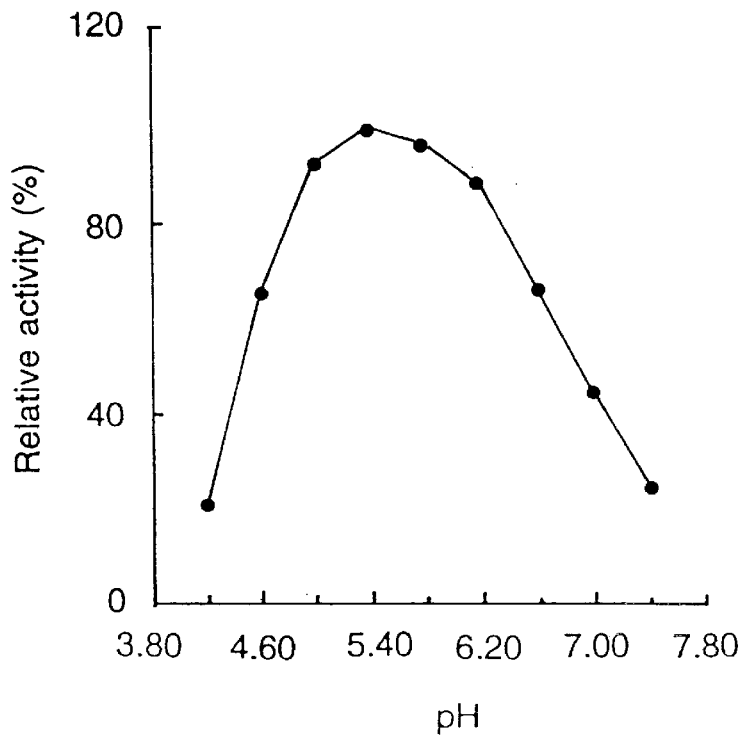
FIG. 3A and FIG. 3B.

The pH profile was determined using the following buffer systems (40° C.): 0.1M sodium acetate (pH 3.8 to 5.4), sodium phosphate (pH 5.8 to 7.8), and diethanolamine-HCl (pH 8.2 and 8.6) with increments of 0.4. The effect of pH on enzyme stability was determined by measuring the residual activity after 24 h incubation at 4° C. (pH 3.0 to 10.2), using the following buffers: glycine-HCl buffer (pH 3.0–3.4); diethanolamine-HCl (pH 9.0); piperazine-HCl (pH 9.4–10.2). [Ranges of other pH buffers were determined using the optimum pH conditions]. As illustrated in FIG. 3A, the protein is active between pH 4.6 and 7.0 (>50% activity), with an optimum between pH 5.5 and 5.8. The protein was stable for at least 24 h when incubated at pH values between 3.8 and 9.8 at 4° C. Incubation at pH 3.0 resulted in approximately 40% activity.

Figure 3B:
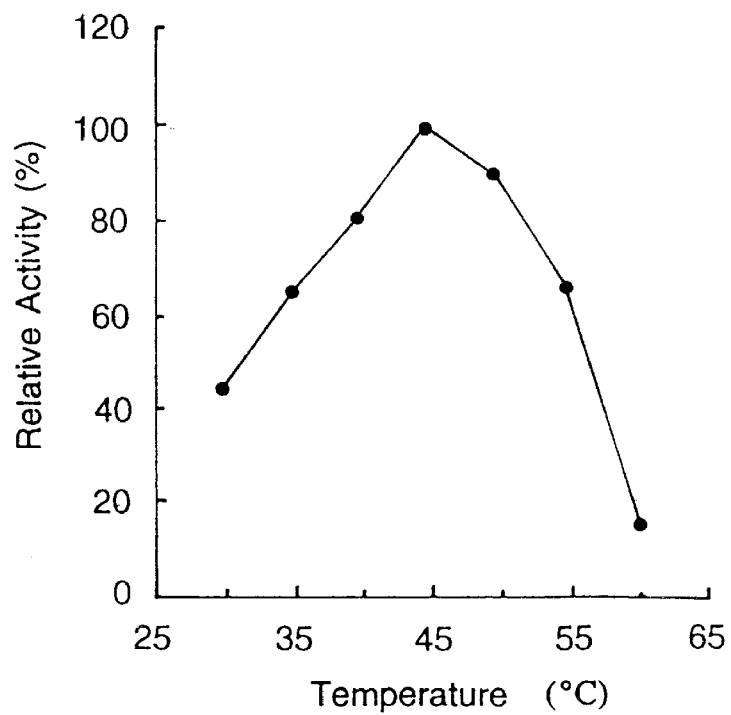

The effect of temperature on xylanase activity was determined by assaying the enzyme at temperatures from 30 to 70° C., with 50° C. increments. Thermostability was measured by incubating the enzyme in 50 mM piperazine HCl buffer (pH 5.5) for 10 min to 24 h at temperatures ranging from 30° to 60° C. with 5° C. increments. Following incubation, the enzyme solution was chilled in an ice bath for 5 min. As illustrated in FIG. 3B, maximum activity occurs at temperatures between 45° C. and 50° C., with decreasing activity above 50° C. No activity loss was observed after 24 h at 40° C. or 45° C. The protein retained 78% activity after 24 h at 50° C. Rapid inactivation occurred at 60° C. with only 50% activity after 1 h.

The effects of various metal ions and reagents on xylanase activity were determined in 50 mM piperazine-HCl, pH 5.5. The enzyme and metal ions or reagents (1 and 3 mM) were preincubated at 22° C. for 10 min; residual activities were measured at 40° C. Controls (no metal ions or reagents) produced 100% activity. As shown in Table 3, $Ca^{++}$, $Mg^{++}$, $Co^{++}$, $Fe^{++}$, $Cs^{++}$, $Zn^{++}$, $Ni^{++}$, $Cd^{++}$, EDTA, and β-mercaptoethanol do not significantly effect xylanase activity, whereas 2-hydroxy-5-bitrobenzylbromide, $Cu^{++}$, $Hg^{++}$, and $Mn^{++}$ are inhibitory. N-bromosuccinimide, SDS, and hydroxymercuribenzoate have a significant inhibitory effect, and cause total inactivation at 1 mM concentrations.

TABLE 3

Effect of Reagents on Endoxylanase from Orpinomyces sp. strain PC-2[a]

| Reagent | Relative activity (%) | |
|---|---|---|
| | 1 mM | 3 mM |
| N-Bromosuccinimide | 0 | 0 |
| 2-Hydroxy-5-nitroxyl-5-nitrobenzyl-bromide | 85.5 | 63.3 |
| SDS | 0 | 0 |
| Hydroxymercuribenzoate | 0 | 0 |
| EDTA | 96.3 | 93.7 |
| β-Mercaptoethanol | 96.7 | 95.4 |
| $Cu^{++}$ | 44.2 | 28.3 |
| $Hg^{++}$ | 32.7 | 11.5 |
| $Mn^{++}$ | 70.8 | 59.3 |

[a]$Ca^{++}$, $Mg^{++}$, $Co^{++}$, $Fe^{++}$, $Cs^{++}$, $Zn^{++}$, $Ni^{++}$, and $Cd^{++}$ had no significant influence at 1 or 3 mM.

The purified enzyme was assayed for the hydrolytic activity against a variety of natural and synthetic substrates. As shown in Table 4, the enzyme has high activity towards xylan substrates and less activity towards polysaccharides such as laminarin, barley β-glucan, and lichenin. No detectable activity was observed towards microcrystalline cellulose, pullulan, mannan, chitin, starch or polygalacturonic acid. The enzyme had no glycosidase or esterase activities. Thus, XynA-1 is more active on soluble xylans, with similar activity towards oat spelts xylan and birchwood xylan. A Lineweaver-Burk plot of the activity over a broad concentration range of water-soluble oat spelts xylan (0.1 to 4.0%) showed that the $K_m$ and $V_{max}$ of this enzyme were 2.15 mg ml$^{-1}$ and 1,770 U/mg protein, respectively.

TABLE 4

Substrate Specificity of Endoxylanase from Orpinomyces sp. strain PC-2[a]

| Substrate | Specific Activity (U mg$^{-1}$ protein) | % |
|---|---|---|
| Water-soluble xylan | 1593.2 | 100 |
| Water-insoluble xylan | 562.4 | 35.5 |
| Oat spelts xylan | 1247.5 | 78.3 |
| Birchwood xylan | 1287.3 | 80.8 |
| Laminarin | 36.6 | 2.3 |
| Lichenin | 49.4 | 3.1 |
| Barley β-glucan | 55.8 | 3.5 |

[a]The following substrates were hydrolyzed at less than 0.5% of the rate of water soluble xylan or hyrolysis of the substrate was undetectable: Avicel, CMC, Gum arabic, pullulan, mannan, chitin, starch, and polygalacluronic acid (1% wt vol$^{-1}$) and PNP-β-D-xylosidase, PNP-β-D-glucosidase, PNP-β-D-cellobiose, PNP-α-L-arabinoside, and PNP-acetate (1 mM).

Hydrolysis products released by the purified xylan from water soluble oat spelts xylan (WSOSX) were separated using thin-layer chromatography (TLC) silica gel plates (Analtech, Inc.,Newark, Del.). Enzyme (1.2 U) was incubated in 50 mM piperazine-HCl buffer, pH 5.5, at 40° C. with 10 mg water soluble oat spelts xylan. Samples were withdrawn at 10 and 30 min, and 1, 2, 4, 18 and 24 hr intervals. Hydrolysis was terminated by placing the samples in boiling water for 5 min. TLC was performed in a solvent system containing chloroform, glacial acetic acid and water (6:7:1, v/v), as described by Lake, B. D. and Goodwin, H. J. (1976) "Chromatographic and electrophoretic techniques," In: *Smith I. and Seakins. J. W. T.* (eds.), Lipids (4th ed.) Pitman Press (Bath, England) vol. 1, pp. 345–366.

Figure 4:
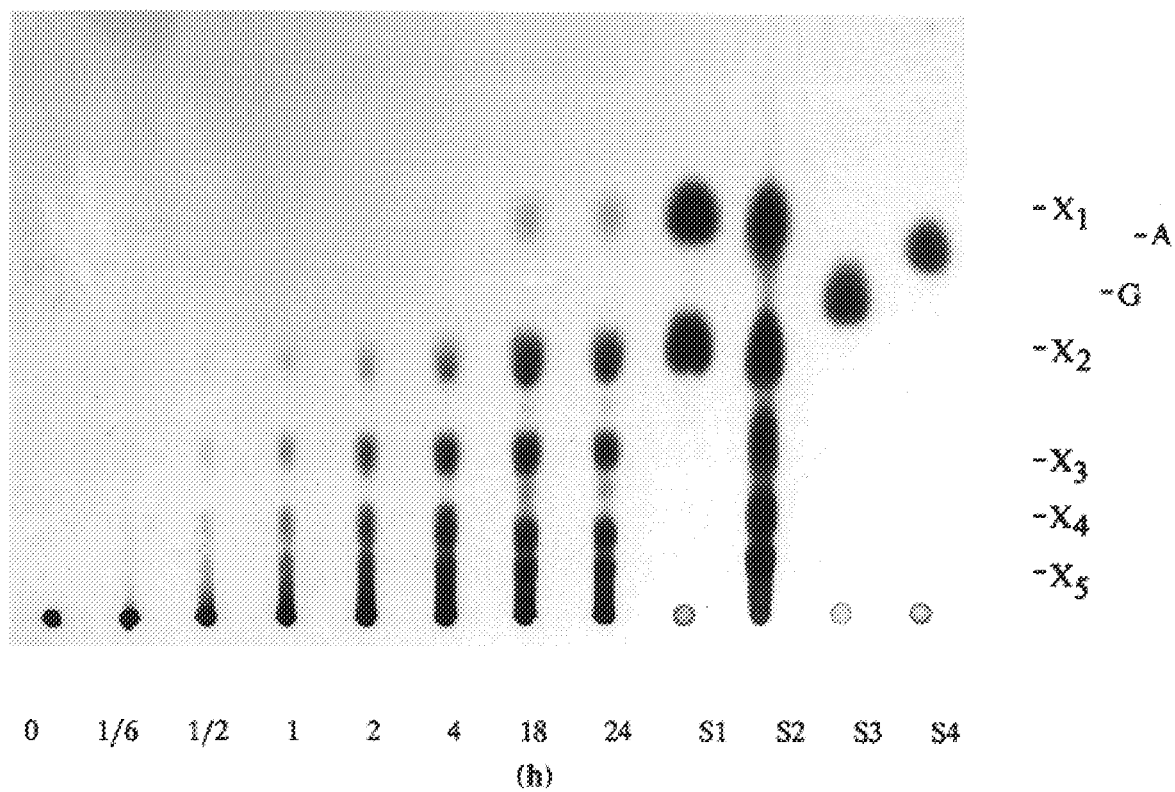
FIG. 4. Thin-layer chromatogram of water-soluble oat spelts xylan degradation products with the purified endoxylanase from Orpinomyces sp. strain PC-2. S1, xylose ($X_1$) and xylobiose ($X_2$); S2, xylose ($X_1$), xylobiose ($X_2$), xylotriose ($X_3$), xylotetraose ($X_4$), and xylopentaose ($X_5$); S3, glucose (G); S4, arabinose (A).

Plates were sprayed with a solution comprising aniline (2 ml), diphenylamine (2 g), acetone (100 ml), and 85% $H_3PO_4$ (15 ml). Sugars were visualized by heating the plate for 15 min at 105° C., as described by Hansen, S. A. (1975) "Thin-layer chromatographic method for identification of oligosaccharides in starch hydrolyzates," *J. Chromatogr.* 105:388–390. Xylose, xylobiose, xylooligosaccharides, glucose, and arabinose were used as standards. The results are shown in FIG. 4. Initially, only xylooligosaccharides were detected. Minor amounts of xylose appeared after about 4 h. The predominant end products from WSOSX hydrolysis were xylobiose, xylotriose, and xylotetraose. No glucose or arabinose was detected among the hydrolysis products of WSOSX, even at 24 h incubation.

was performed following the Stratagene instruction manual, except that the upper agar layer contained 5 mM isopropyl-α-D-thiogalactoside (IPTG) and 0.2% (w/v) remazol brilliant blue R-D-xylan. During the screening of $5 \times 10^4$ plaque forming units (pfu), 22 plaques had a clear zone. Ten of these clear zones were picked and subjected to a second round of screening. Pure clones were isolated after the second-round screening and converted into pBluescript by in vivo excision.

Restriction mapping and sequencing demonstrated that all ten clones had a common fragment. A clone (pOX8, XynA) containing a cDNA insert of 1.2 kb was sequenced and an open reading frame (ORF) was identified (SEQ ID NO:1). A start codon (ATG) 97 bp downstream of the 5' end of XynA

TABLE 5

Properties of Endoxylanases from Various Fungi

| Organism | $M_r$ (kDa) | pI | Optimum pH | Optimum Temp. (°C.) | End Products | $K_m$ (mg ml$^{-1}$) | $V_{max}$ (U mg$^{-1}$ protein) | CMCase (% of xylanase activity) | Reference |
|---|---|---|---|---|---|---|---|---|---|
| *Piromyces* sp. strain E2 | 12.5 | 9.1 | 6.0 | 50 | $X_2, X_3, X_n$ | 3.0 | 2600 | U.D.[b] | Teunissen et al., 1993 |
| *N. frontalis* MCH3 | 45 | N.D.[a] | 5.5 | 55 | $X_4, X_n$ | 1.22 | 37 | 38 | Gomez de Segura and Fevre, 1993 |
| *N. frontalis* RK21 | 70 | N.D. | 6.0 | 55 | $X_4, X_n$ | 2.5 | 317 | 28 | |
|  | 30 | 5.0–10.0 | 6.0–6.6 | 50 | $X_2-X_4, X_n$ | N.D. | 103 | U.D. | Garcia-Campayo et al., 1993 |
| *Orpinomyces* sp. strain PC-2 | 29 | 8.2 | 5.4 | 45 | $X_1-X_5$ | 2.15 | 1770 | U.D. | this work |

[a]not determined
[b]undetected

Example 2

Cloning of XynA 2

Strains, vectors, and cultivation conditions. Orpinomyces sp. strain PC-2 was isolated from the rumen of a cow and cultured as described by Borneman, W. S., et al. (1989) "Fermentation products and plant cell wall degrading enzymes produced by monocentric and polycentric anaerobic fungi," *Appl. Environ. Microbiol.* 55:1066–1073. Cultures were grown at 39° C. on 0.2% (w/v) oat spelt xylan (OSX) or 0.2% Avicel (w/v) as carbon sources, for 4 days. *E. coli* strains used in this study include SURE, XL's-Blue, JM109 and vectors pRSET and pBluescript (Stratagene Cloning Systems, La Jolla, Calif.).

Isolation of RNA from Orpinomyces sp. strain PC-2. For isolation of RNA as template for cDNA library construction, cells were grown for 4 days on 0.2% (w/v) OSX as carbon source. Disruption of cells and extraction of RNA were performed using an RNA isolation kit (Stratagene Cloning Systems, La Jolla) following the manufacturer's instructions, with the exception that the cells were broken by shaking (100 rpm) in a water bath at 60° C. with glass beads (212–300μ in size, Sigma Chemical Co., St. Louis, Mo.). Poly(A) RNA was prepared from total RNA by chromatography on oligo (dT) cellulose (Boehringer Mannheim Co., Indianapolis, Ind.).

A λ-ZAPII cDNA library comprising DNA inserts between 0.4 and 9.0 kb was constructed and used for xylanase positive plaque screening. Screening of the library was identified, which began an ORF encoding a polypeptide of 362 amino acids. The G+C content of the coding region was 42%, with the non-coding 5' and 3' regions extremely A+T rich. The encoded polypeptide has a molecular mass of 39,542 Da with a N-terminal peptide rich in hydrophobic residues, which might serve as a membrane translocational signal peptide for the secretion of the xylanase.

Homology of the sequence with other xylanases: The deduced amino acid sequence of XynA-2 was used to search for homologous sequences in the SWISS-PROT data base. This sequence had homology with the following fungal and bacterial proteins: xylanase catalytic domain A and B of *Neocallimastix partriciarum* and *N. frontalis* (80–84%), xylanases of *Clostridium acetobutylicum* (41.8%), *C. stercorarium* (38.0%), *Trichoderma reesei* (38.8%), *Ruminococcus flavefaciens* (37.8%), and *Bacillus pumilus* (40.6%). It is of particular interest to compare the xylanase genes from the anaerobic fungi. The sequences encoding xylanases of *N. patriciarum* (Gilbert, H. J., et al. (1992), "Homologous catalytic domains in rumen fungal xylanase: evidence for gene duplication and prokaryotic origin," *Mol. Microbiol.* 6:2065–2072) and *N. frontalis* (Genbank Accession Number X82266) are 99% homologous. Both have two highly homologous catalytic domains (A and B) and two C-terminal repeated regions. Each of the two catalytic domains are about 220 amino acids and each of the two C-terminal repeated regions have 40 amino acids. Short peptides (very rich in hydroxyl side chain residues Thr and Ser) appear between the two catalytic domains as well as the second catalytic domain and the first C-terminal repeated region. In contrast to the Neocallimastix xylanase sequence, XynA-2 of Orpinomyces PC-2 has only one catalytic domain. In addition, the catalytic domains of Orpinomyces XynA-2 and Neocallimastix xylanases are less than 85% homologous. The Orpinomyces XynA-2 also has two C-terminal repeated domains which are highly homologous to the corresponding regions of the two Neocallimastix xylanases and one *N. patriciarum* endoglucanase (Zhou, L. P., et al. (1994) "Intronless celB from the anaerobic fungus *Neocallimastix patriciarum* encodes a modular family A endoglucanase" *Biochem. J.* 297:359–364.

Figure 6:
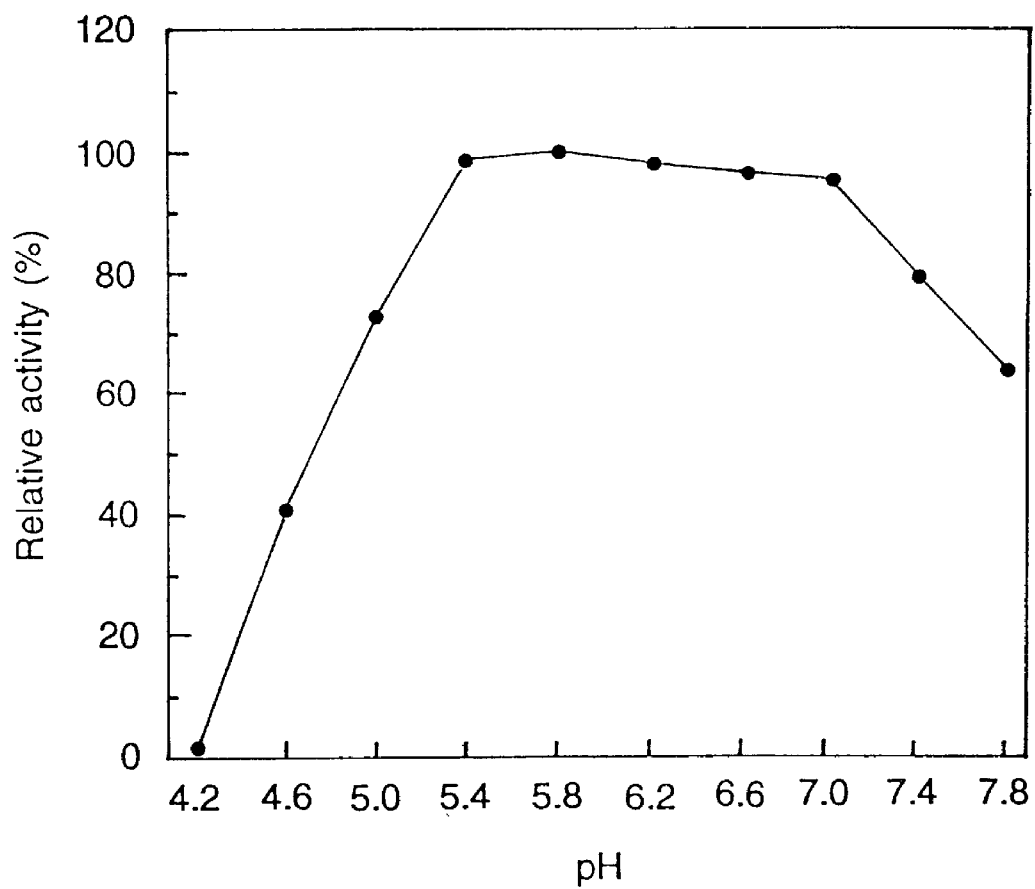
FIG. 6. Effect of pH on the activity of Orpinomyces sp. strain PC-2 xylanase XynA-2 isolated from the periplasmic space of *E. coli*.
Figure 7:
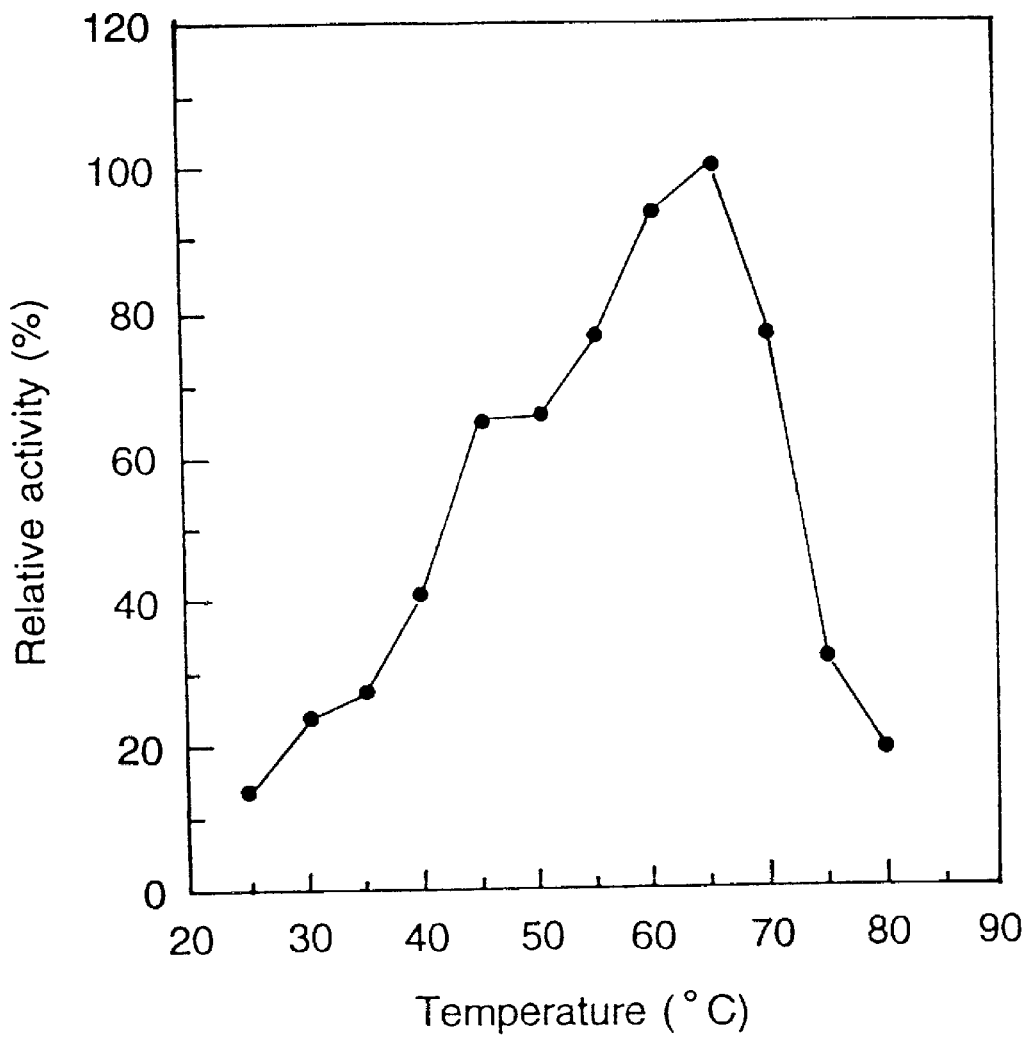
FIG. 7. Temperature optimum of Orpinomyces sp. strain PC-2 xylanase XynA-2. Solubilized OSX (200 $\mu$l; 1.0% in 50 mM Pipes buffer, pH 6.8) was pre-incubated at various temperatures for 30 seconds. Enzyme (20 μl) was added and the reaction mixture was incubated for 5 min. Reactions were terminated by adding 1 ml DNS reagent and cooling in an ice bath. Reducing sugars were measured using the DNS reagent as described in Miller, G. L. (1959) "Use of dinitrosalicylic acid reagent for determination of reducing sugars," *Anal. Chem.* 31:426–428.

*E. coli* harboring pOX8 was grown in Luria-Bertani medium and induced by IPTG. Cells were subjected to osmotic shock, as described by Neu, H. C. and Heppel, L. A. (1965) "The release of enzymes from *Escherichia coli* by osmotic shock and during the formation of spheroplast," *J. Biol. Chem.* 240:3685–3692, followed by sonication. Over 70% of the total xylanase activity was recovered in the periplasmic fraction, which indicates that the mature enzyme was secreted into the periplasmic space of *E. coli* cells. The effect of pH and temperature on the activity was determined. The enzyme had high activity in broad ranges of pH (5.6–7.8; FIG. 6) and temperature (40°–70° C.; FIG. 7). To obtain higher levels of expression, the Orpinomyces xynA-2 gene was inserted in frame into pRSET plasmid with a T7 promoter. To facilitate the in-frame insertion, XynA-2 was amplified by polymerase chain reactions with two primers containing EcoRI and BamHI restriction sites. This clone has at least 10-fold greater xylanase activity than pOX8 after induction by IPTG.

Further modifications of the invention herein disclosed will occur to persons skilled in the art who have the benefit of this disclosure, and all such modifications are deemed to be within the spirit and scope of the invention as defined by the appended claims.

We claim:

1. An isolated recombinant DNA molecule comprising a nucleotide sequence encoding a xylanase protein from Orpinomyces, wherein said nucleotide sequence is at least 90% homologous to a nucleotide sequence as given in SEQ ID NO:1 nucleotides 169–1185.

2. The isolated recombinant DNA molecule of claim 1 wherein said nucleotide sequence encodes a XynA-2 protein that has an amino acid sequence as given in SEQ ID NO:2 from amino acid 25 through amino acid 362 or a functionally equivalent sequence with at least 90% homology thereto.

3. The isolated recombinant DNA molecule of claim 2 wherein said XynA-2 protein is encoded by the nucleotide sequence as given in SEQ ID NO:1 from about nucleotide 169 through nucleotide 1185 or a functionally equivalent sequence with at least 90% homology thereto.

4. The isolated recombinant DNA molecule of claim 2 wherein said XynA-2 protein has an amino acid sequence as given in SEQ ID NO:2 from amino acid 20 through amino acid 362 or a functionally equivalent sequence with at least 90% homology thereto.

5. The isolated recombinant DNA molecule of claim 4 wherein said XynA-2 protein is encoded by the nucleotide sequence as given in SEQ ID NO:1 from nucleotide 154 through nucleotide 1185 or a functionally equivalent sequence with at least 90% homology thereto.

6. The isolated recombinant DNA molecule of claim 2 wherein said XynA-2 protein has an amino acid sequence as given in SEQ ID NO:2 from amino acid 15 through amino acid 362 or a functionally equivalent sequence with at least 90% homology thereto.

7. The isolated recombinant DNA molecule of claim 6 wherein said XynA-2 protein is encoded by the nucleotide sequence as given in SEQ ID NO:1 from nucleotide 139 through nucleotide 1185 or a functionally equivalent sequence with at least 90% homology thereto.

8. The isolated recombinant DNA molecule of claim 2 wherein said XynA-2 protein has an amino acid sequence as given in SEQ ID NO:2 from amino acid 1 through amino acid 362 or a functionally equivalent sequence with at least 90% homology thereto.

9. The isolated recombinant DNA molecule of claim 8 wherein said XynA-2 protein is encoded by the nucleotide sequence as given in SEQ ID NO:1 from nucleotide 97 through nucleotide 1185 or a functionally equivalent sequence with at least 90% homology thereto.

10. The isolated recombinant DNA molecule of claim 2 additionally comprising DNA encoding a signal peptide immediately upstream of and operably linked to the nucleotide sequence encoding said XynA-2 protein.

11. The isolated recombinant DNA molecule of claim 10 wherein said signal peptide is an *Aureobasidium pullulans* xylanase II (APX-II) signal peptide.

12. An *Escherichia coli* cell comprising the recombinant DNA molecule of claim 2.

13. A *Saccharomyces cerevisiae* cell comprising the recombinant DNA molecule of claim 2.

14. An *Aspergillus nidulans* cell comprising the recombinant DNA molecule of claim 2.

15. A *Trichoderma reesei* cell comprising the recombinant DNA molecule of claim 2.

16. A recombinant host cell comprising the recombinant DNA molecule of claim 2 wherein said host cell is selected from the group consisting of Pichia, Streptomyces and Bacillus.

17. A method of using a DNA molecule comprising a nucleotide sequence encoding a xylanase protein from Orpinomyces to produce the xylanase protein in a host cell other than Orpinomyces sp. strain PC-2, wherein said nucleotide sequence is at least 90% homologous to a nucleotide sequence as given by SEQ ID NO:1, nucleotides 169–1185, said method comprising the steps of:

(a) infecting or transforming said host cell capable of expressing a xylanase coding region with a vector comprising a promoter active in said host cell wherein said promoter is operably linked to the coding region for said xylanase; and (b) culturing the infected or transformed cell under conditions suitable for expression of said xylanase.

18. The method of claim 17 wherein said host cell is an *Escherichia coli* cell.

19. The method of claim 17 wherein said host cell is a *Saccharomyces cerevisiae* cell.

20. The method of claim 17 wherein said host cell is an *Aspergillus nidulans* cell.

21. The method of claim 17 wherein said host cell is a *Trichoderma reesei* cell.

22. The method of claim 17 wherein said host cell is selected from the group consisting of Pichia, Streptomyces and Bacillus.

23. The method of claim 17 wherein said vector further comprises a nucleotide sequence encoding a signal peptide operably linked between said promoter and said coding region.

24. The method of claim 23 wherein said peptide is an *Aureobasidium pullulans* xylanase II (APX-II) signal peptide.

25. The method of claim 17 wherein said DNA molecule encodes a xylanase XynA-2 protein having an amino acid sequence as set forth in SEQ ID NO:2 from amino acid 25 through amino acid 362 or a functionally equivalent sequence with at least 90% homology thereto.

26. The method of claim 17 wherein said coding region for said xylanase XynA-2 protein has the nucleotide sequence as set forth in SEQ ID NO:1 from nucleotide 169 through nucleotide 1185 or a functionally equivalent sequence with at least 90% homology thereto.

27. The method of claim 17 wherein said DNA molecule encodes a xylanase XynA-2 protein having an amino acid sequence as set forth in SEQ ID NO:2 from amino acid 20 through amino acid 362 or a functionally equivalent sequence with at least 90% homology thereto.

28. The method of claim 17 wherein said coding region for said xylanase XynA-2 protein has the nucleotide sequence as set forth in SEQ ID NO:1 from nucleotide 154 through nucleotide 1185 or a functionally equivalent sequence with at least 90% homology thereto.

29. The method of claim 17 wherein said DNA molecule encodes a xylanase XynA-2 protein having an amino acid sequence as set forth in SEQ ID NO:2 from amino acid 15 through amino acid 362 or a functionally equivalent sequence with at least 90% homology thereto.

30. The method of claim 17 wherein said coding region for said xylanase XynA-2 protein has the nucleotide sequence as set forth in SEQ ID NO:1 from nucleotide 139 through nucleotide 1185 or a functionally equivalent sequence with at least 90% homology thereto.

31. The method of claim 17 wherein said DNA molecule encodes a xylanase XynA-2 protein having an amino acid sequence as set forth in SEQ ID NO:2 from amino acid 1 through amino acid 362 or a functionally equivalent sequence with at least 90% homology thereto.

32. The method of claim 17 wherein said coding region for said xylanase XynA-2 protein has the nucleotide sequence as set forth in SEQ ID NO:1 from nucleotide 97 through nucleotide 1185 or a functionally equivalent sequence with at least 90% homology thereto.

* * * * *

UNITED STATES PATENT AND TRADEMARK OFFICE
CERTIFICATE OF CORRECTION

PATENT NO. : 5,824,533

DATED : October 20, 1998

INVENTOR(S) : Li et al.

It is certified that error appears in the above-identified patent and that said Letters Patent is hereby corrected as shown below:

On the title page: Item [56]

On Page 1, in Other Publications, in the second column, under "Innis et al.", please delete
"*Sacchromyces*" and replace with --*Saccharomyces*--.
On Page 2, in Other Publications, in the first column, under "Marten, M. and J-H Seo", please delete
"*Sacchromyces*" and replace with --*Saccharomyces*--.
On Page 2, in Other Publications, in the second column, under "Mounfort, D.O. and R.A. Asher", please
delete "*Micronbiol.*" and replace with --*Microbiol.*--.
On Page 2, in Other Publications, in the second column, under "Teunissen et al.", please delete
"train" and replace with --strain--.
In column 3, line 64, please delete "a pheromone" and replace with --α pheromone--.
In column 4, line 39, please delete "(1 $\mu$)." and replace with --(1 $\mu$g).--.
In column 7, line 35, please delete "w=" and replace with --W=--.
In column 9, line 49, please delete "p-nitrophenyl-α-xyloside," and replace with --p-nitrophenyl-β-xyloside,--.
In column 13, line 64, please delete "0β-glucosidase" and replace with --β-glucosidase--.
In column 15, line 47, please delete "50° C." and replace with --5° C.--.
In column 18, line 3, please delete "α-D-thiogalactoside" and replace with --β-D-thiogalactoside--.
In column 26, line 4, please insert --host-- in between "transformed" and "cell".
In column 26, line 22, please insert --signal-- in between "said" and "peptide".

Signed and Sealed this

Thirtieth Day of March, 1999

*Attest:*

*Attesting Officer*

Q. TODD DICKINSON

*Acting Commissioner of Patents and Trademarks*